(12) United States Patent
Raharja

(10) Patent No.: US 12,175,661 B2
(45) Date of Patent: Dec. 24, 2024

(54) METHOD OF PROCESSING AN IMAGE OF TISSUE, A SYSTEM FOR PROCESSING AN IMAGE OF TISSUE, A METHOD FOR DISEASE DIAGNOSIS AND A DISEASE DIAGNOSIS SYSTEM

(71) Applicant: PANAKEIA TECHNOLOGIES LIMITED, Cambridge (GB)

(72) Inventor: Muhammad Pandu Raharja, London (GB)

(73) Assignee: PANAKEIA TECHNOLOGIES LIMITED, Cambridge (GB)

( * ) Notice: Subject to any disclaimer, the term of this patent is extended or adjusted under 35 U.S.C. 154(b) by 334 days.

(21) Appl. No.: 17/442,328

(22) PCT Filed: Mar. 25, 2020

(86) PCT No.: PCT/EP2020/058414
§ 371 (c)(1),
(2) Date: Sep. 23, 2021

(87) PCT Pub. No.: WO2020/193651
PCT Pub. Date: Oct. 1, 2020

(65) Prior Publication Data
US 2022/0156926 A1 May 19, 2022

(30) Foreign Application Priority Data
Mar. 26, 2019 (EP) .................................. 19165346

(51) Int. Cl.
*G06T 7/00* (2017.01)
*A61B 90/20* (2016.01)
(Continued)

(52) U.S. Cl.
CPC ............ *G06T 7/0012* (2013.01); *A61B 90/20* (2016.02); *G06F 18/214* (2023.01); *G06F 18/40* (2023.01);
(Continued)

(58) Field of Classification Search
None
See application file for complete search history.

(56) References Cited

U.S. PATENT DOCUMENTS

| | | | |
|---|---|---|---|
| 7,646,905 B2 | 1/2010 | Guittet et al. | |
| 10,002,311 B1 * | 6/2018 | Garnavi | G06N 3/044 |

(Continued)

OTHER PUBLICATIONS

European Search Report for corresponding Application No. EP19165346.8, dated Oct. 9, 2019, 13 pages.
(Continued)

*Primary Examiner* — Leon Flores
(74) *Attorney, Agent, or Firm* — Dority & Manning, P.A.

(57) ABSTRACT

A computer implemented method of processing an image of tissue, comprising: inputting image data comprising a plurality of pixels into a first trained model, the first trained model generating a value corresponding to each of a plurality of pixels representing a feature relevant to disease diagnosis; wherein the first trained model comprises a convolutional neural network comprising a layer in which a first filter and a second filter are applied, at least one of the first filter and the second filter comprising a dilated convolution, wherein the output of the first filter and the second filter are combined and input into the subsequent layer.

17 Claims, 18 Drawing Sheets

(51) Int. Cl.
| | |
|---|---|
| G06F 18/214 | (2023.01) |
| G06F 18/40 | (2023.01) |
| G06N 3/08 | (2023.01) |
| G06T 7/11 | (2017.01) |
| G06T 7/73 | (2017.01) |
| G16H 50/20 | (2018.01) |

(52) U.S. Cl.
CPC .................. *G06N 3/08* (2013.01); *G06T 7/11* (2017.01); *G06T 7/73* (2017.01); *G16H 50/20* (2018.01); *G06T 2200/24* (2013.01); *G06T 2207/10056* (2013.01); *G06T 2207/20081* (2013.01); *G06T 2207/20084* (2013.01); *G06T 2207/30096* (2013.01)

(56) References Cited

U.S. PATENT DOCUMENTS

| | | | |
|---|---|---|---|
| 10,049,450 | B2 | 8/2018 | Madabhushi et al. |
| 2004/0013292 | A1 | 1/2004 | Raunig |
| 2010/0111396 | A1 | 5/2010 | Boucheron |
| 2011/0274338 | A1 | 11/2011 | Park et al. |
| 2016/0253466 | A1 | 9/2016 | Agaian et al. |
| 2016/0350919 | A1 | 12/2016 | Steigauf et al. |
| 2017/0175169 | A1 | 6/2017 | Lee et al. |
| 2017/0357879 | A1* | 12/2017 | Odaibo .................. G06N 3/044 |
| 2018/0108139 | A1 | 4/2018 | Abramoff et al. |
| 2020/0085290 | A1* | 3/2020 | Wang ........................ A61B 3/12 |
| 2021/0035689 | A1* | 2/2021 | Liu ........................ G06F 18/214 |
| 2021/0224977 | A1* | 7/2021 | Jia ........................... G06F 18/24 |

OTHER PUBLICATIONS

PCT International Report on Patentability for corresponding Application No. PCT/EP/2020/058414, mailed on Oct. 7, 2021, 14 pages.

Chen et al., "Computer-aided prognosis on breast cancer with hematoxylin and eosin histopathology images: A review", Tumor Biology, Mar. 2017, 12 pages.

LeCun et al., "Deep learning", Nature, May 28, 2015, vol. 521, pp. 436-444.

MDAnderson.org, "Detailed Pathology Methods for Using Residual Cancer Burden", https://www.mdanderson.org/education-and-research/resources-for-professionals/clinical-tools-and-resources/clinical-calculators/calculators-rcb-pathology-protocol2.pdf, retrieved on Feb. 3, 2022, 7 pages.

Naumov et al., "Parallel Depth First on GPU", NVIDIA On-Demand, https://on-demand.gputechconf.com/gtc/2017/presentation/s7469-maxim-naumov-parallel-depth-first-on-gpu.pdf, retrieved on Feb. 3, 2022, 60 pages.

Ruder, "An Overview of gradient descent optimization algorithms*", arXiv:1609.04747v2, Jun. 15, 2017, 14 pages.

Wikipedia.org, "Depth-first search", https://en.wikipedia.org/w/index.php?title=Depth-first_search&oldid=1028790980M, retrieved on Feb. 3, 2022, 7 pages.

PCT International Search Report for corresponding PCT Application No. PCT/EP2020/058414, mailed on May 29, 2020, 7 pages.

Pereira et al., "Brain Tumor Segmentation Using Convolutional Neural Networks in MRI Images," IEEE Transactions On Medical Imaging, vol. 35, No. 5, May 2016, pp. 1240-1251.

Dadashzadeh et al., "Multi-Level Contextual Network for Biomedical Image Segmentation," Cornell University Library, 201 Olin Library Cornell University Ithaca, NY, Sep. 30, 2018, 7 pages.

Sarvadevabhatla et al., "Expresso: A user-friendly GUI for Designing, Training and Exploring Convolutional Neural Networks", May 25, 2015, 4 pages.

Delakis et al.: "Convolutional Face Finder: A Neural Architecture for Fast and Robust Face Detection," IEEE Transactions on Pattern Analysis and Machine Intelligence, vol. 26, No. 11, Nov. 2004, pp. 1408-1423.

Wang et al., "Histopathological Image Classification with Bilinear Convolutional Neural Networks," 2017 $39^{th}$ Annual International Conference of The IEEE Engineering In Medicine And Biology Society (EMBC), Jul. 11, 2017 pp. 4050-4053.

Tzelepi et al., "Relevance Feedback in Deep Convolutional Neural Networks for Content Based Image Retrieval," SETN '16: Proceedings of the 9th Hellenic Conference on Artificial Intelligence, May 2016, 7 pages.

Indian Search Report for corresponding Application No. 202117047715, dated Mar. 1, 2024, 8 pages.

European Office Action for corresponding Application No. 20712395.1, dated Jul. 2, 2024, 6 pages.

T. Schlegl et al., "Predicting Semantic Descriptions from Medical Images with Convolutional Neural Networks", Austria, Jun. 23, 2015, pp. 437-448.

* cited by examiner

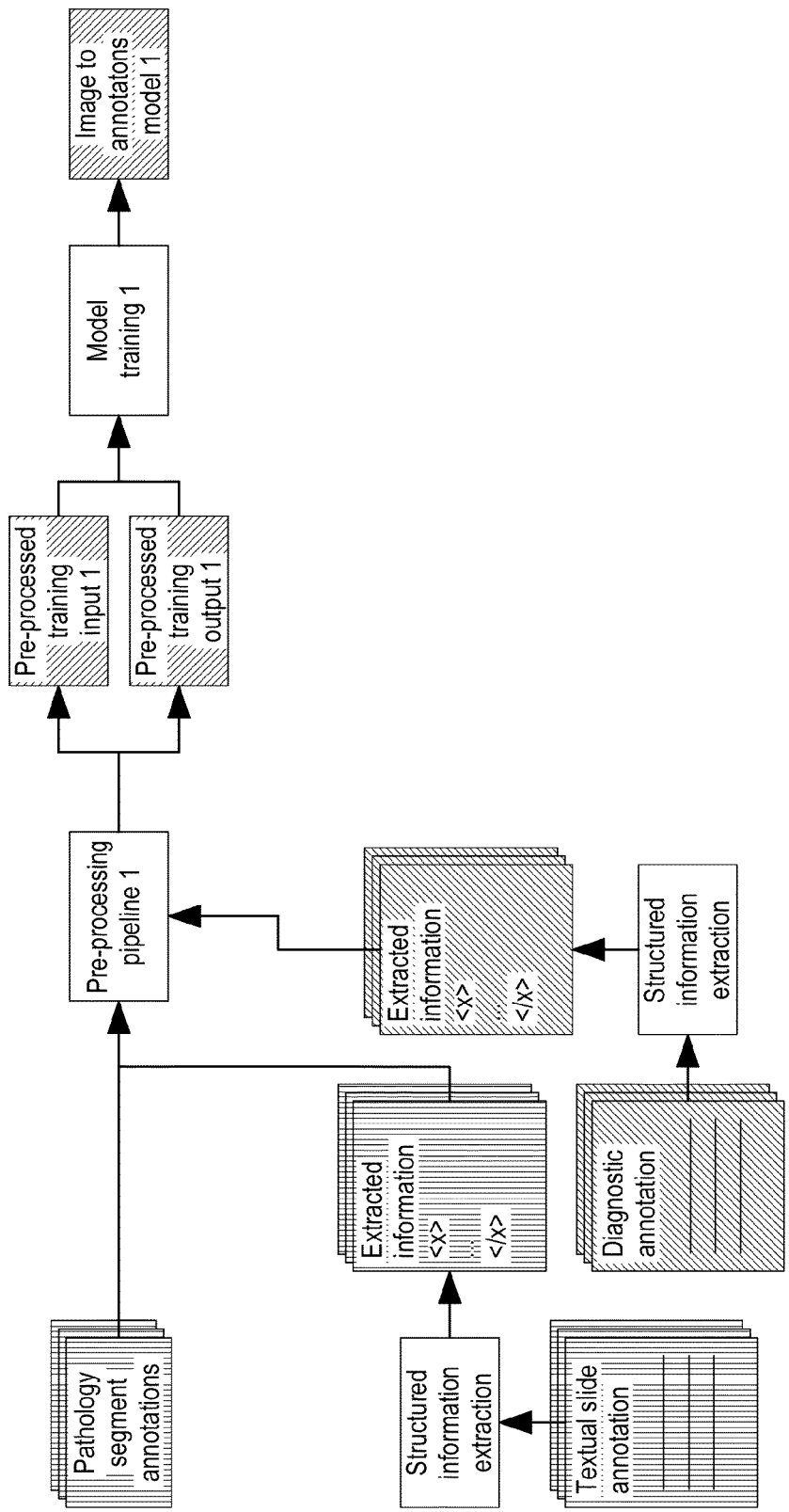
Fig. 3(b)(ii)

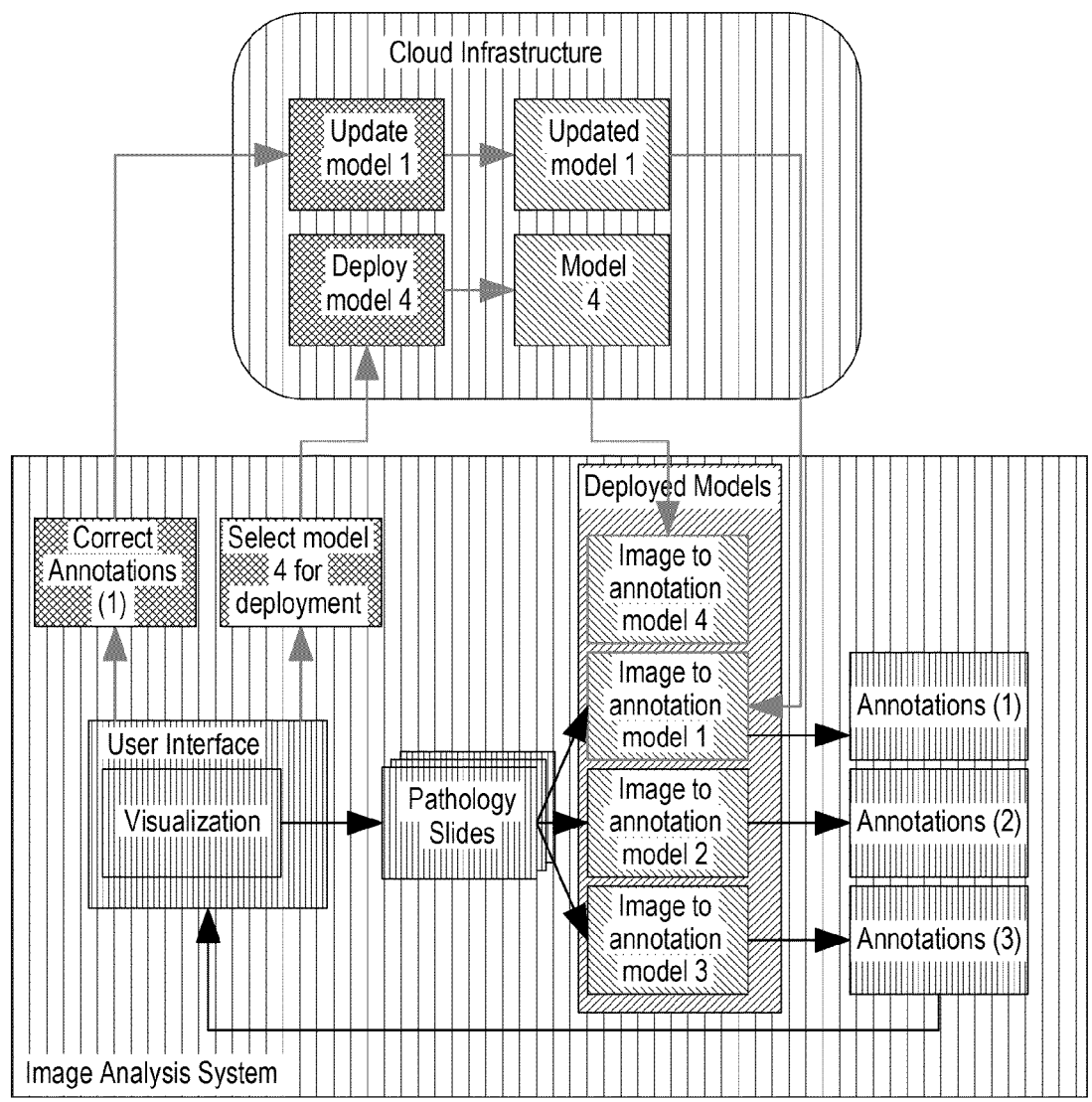
Fig. 3(b)(iii)

METHOD OF PROCESSING AN IMAGE OF TISSUE, A SYSTEM FOR PROCESSING AN IMAGE OF TISSUE, A METHOD FOR DISEASE DIAGNOSIS AND A DISEASE DIAGNOSIS SYSTEM

CROSS-REFERENCE TO RELATED APPLICATIONS

This application is a U.S. national phase entry of International Application number PCT/EP2020/058414 filed on Mar. 25, 2020, which, in turn, is based upon and claims the benefit of priority from prior European Application number 19165346.8 filed on Mar. 26, 2019, the entire contents of both of which are incorporated herein by reference.

FIELD

The present invention relates to a computer implemented method of processing an image of tissue, a system for processing an image of tissue, a computer implemented method for disease diagnosis, and a disease diagnosis system.

BACKGROUND

Processing of images of tissue enables the diagnosis of diseases in many use cases. For example, recognition of physical patterns on a histopathological sample is performed to determine and characterise cancer.

In a manual process, a histopathologist looks under a microscope at the whole sample and manually makes notes on visual diagnosis information such as: regions of the slide corresponding to particular features, for example regions corresponding to nuclei, dividing cells, tubules, regions of various types of cancer tissues (e.g. benign, in-situ, or metastatic); cancer tissue differentiation (grading); invasiveness; tumour margin (i.e. the existence of tumour on the edge of the sample); mitotic rate; and/or cancer grading for example. A diagnosis is made based on this information. Non-visual information such as the patient's age and sex may also be taken into account to give the diagnosis.

In a digital histopathology workflow, a digital image is shown to a histopathologist on a screen, for example using web browser. Again, the histopathologist conducts the analysis by gathering information based on the visual patterns in the image of the tissue. The analysis can be performed using an annotation tool, such as Aperio ImageScope for example, allowing the histopathologist to mark-up regions of the image corresponding to the visual features.

In both cases, histopathologists need to recognise complex patterns. A whole slide image may be around 60 000 pixels by 60 000 pixels in size for example. For every patient case, a histopathologist may be presented with tens of such slides. Given the scale and the number of the images, histopathologists spend large amounts of time (often days) analysing the images. Furthermore, the resulting accuracy may be anywhere between 60% and 90%. The qualitative nature of the analysis relies hugely on the experience of the analysing experts, with newer histopathologists performing significantly worse than more senior histopathologists.

There is a continuing need to improve the speed and accuracy of the processing of images of tissue.

BRIEF DESCRIPTION OF FIGURES

Systems and methods in accordance with non-limiting embodiments will now be described with reference to the accompanying figures in which:

FIG. 3(b)(ii) is a schematic illustration of a method of training an image processing system in accordance with an embodiment;

FIG. 3(b)(iii) is a schematic illustration of a system in accordance with an embodiment;

DETAILED DESCRIPTION

Figure 1A:
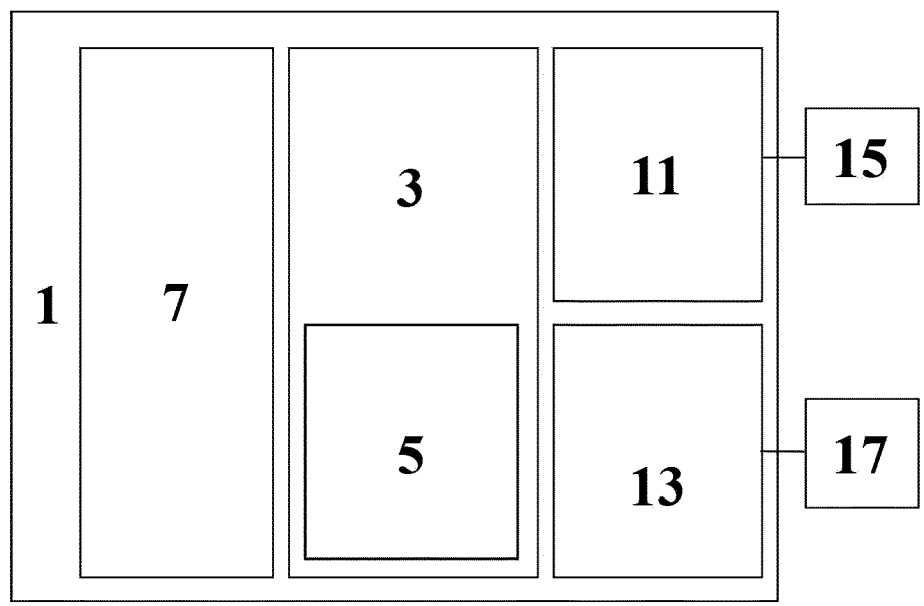
FIG. 1(a) is a schematic illustration of a system in accordance with an embodiment.

According to an embodiment, there is provided a computer implemented method of processing an image of tissue, comprising:
inputting image data comprising a plurality of pixels into a first trained model, the first trained model generating a value corresponding to each of a plurality of pixels representing a feature relevant to disease diagnosis;
wherein the first trained model comprises a convolutional neural network comprising a layer in which a first filter and a second filter are applied, at least one of the first filter and the second filter comprising a dilated convolution, wherein the output of the first filter and the second filter are combined and input into the subsequent layer.

The first trained model classifies each of a plurality of pixels to segment the image according to a feature relevant to disease diagnosis. In an embodiment, each input pixel is classified. The model performs semantic image segmentation, whereby each pixel is classified into one of a set of categories. The categories correspond to one or more features relevant to disease diagnosis. There may be a single category.

In an embodiment, the method of image processing automatically analyses a scanned whole slide image, outputting relevant information enabling a histopathologist to make a diagnosis. The method provides a reduction in the time taken to provide the information. For example, using the above described method, the time taken to provide the enhanced image information may be less than one hour, or even less than 20 minutes, depending on the use case.

Using a first trained model comprising a CNN means that the image data (pixel data) may be inputted directly into the model. Including a dilated convolution provides a wider field of view without increase in computational cost, i.e. without increasing the number of parameters.

In an embodiment, the first convolution is a dilated convolution having a first dilation factor and the second convolution is a dilated convolution having a second dilation factor. The first dilation factor and the second dilation factor are greater than 1 and are different values. Including multiple dilated convolutions having different dilation factors means that the model learns information relating to local and non-local features. Including the multiple dilated convolutions having different dilation factors in one layer means that the model learns correlation of local and non-local information, allowing learning of higher order spatial context.

In an embodiment, the convolutional neural network comprises at least one skip connection. The convolutional neural network comprises a first layer configured to generate an output having a dimension smaller than the output of a previous layer, and a second layer subsequent to the first layer, wherein the input to the second layer is generated from the input to the first layer or a layer prior to the first layer and the output of the layer prior to the second layer. This provides additional context through the model.

In an embodiment, the method further comprises:
receiving modified data generated by a user editing one or more output values via a graphical user interface;
updating the first trained model using the modified data to improve performance.

Augmented training data may be generated from the modified data. For example, the method may further comprise generating multiple versions of the modified data and updating the first trained model using the multiple versions to improve performance.

According to another embodiment, there is provided a computer implemented method of processing an image of tissue, comprising:
inputting image data into a first trained model comprising a convolutional neural network, the first trained model generating a first set of output data representing a feature of the image relevant to disease diagnosis;
inputting image data into a second trained model comprising a convolutional neural network, the second trained model generating a second set of output data representing a feature of the image relevant to disease diagnosis;
combining the first set of output data and the second set of output data;
generating diagnostic information from the combined data using a third trained model.

By splitting the method into two stages, comprising separate models, the output diagnostic information from the second stage is explainable. An expert user can refer to the image labels output from the first stage to check the validity of the output diagnostic information from the second stage. By feeding the information from each model in the first stage in parallel into the second stage, error propagation is avoided.

The image data may be obtained from a histopathological slide for example.

The values may indicate one of the following features: regions of interest in the image, coordinates of dividing cells, or segments of various tissues.

In an embodiment, the diagnostic information comprises one or more of: a cancer tissue nucleation index, a mitotic index, a grading, an indication of tumour size, a metastatic index, or a nodal index.

According to another embodiment, there is provided a computer implemented method of disease diagnosis, comprising a method of processing an image of tissue according to any preceding claim, further comprising generating a final diagnosis from the diagnostic information and context information using a fourth trained model.

According to another embodiment, there is provided a computer implemented method of training a system for processing an image of tissue, comprising:
inputting training image data comprising a plurality of pixels into a first model, the first model generating a value corresponding to each of a plurality of pixels representing a feature relevant to disease diagnosis;
wherein the first model comprises a convolutional neural network comprising a layer in which a first filter and a second filter are performed, at least one of the first filter and the second filter being a dilated convolution, wherein the output of the first filter and the second filter are combined and input into the subsequent layer;
training the first model using training data labels.

According to another embodiment, there is provided a computer implemented method of training a system for processing an image of tissue, comprising:
inputting training image data into a first model comprising a convolutional neural network, the first model generating a first set of output data representing a feature of the image relevant to disease diagnosis;
inputting training image data into a second model comprising a convolutional neural network, the second model generating a second set of output data representing a feature of the image relevant to disease diagnosis;
generating diagnostic information from training data using a third model;
training the first model using training data labels;
training the second model using training data labels;
training the third model using training data labels.

According to another embodiment, there is provided a system for processing an image of tissue, comprising:
an input;
an output;
a processor configured to:
input received image data comprising a plurality of pixels into a first trained model, the first trained model generating a value corresponding to each of a plurality of pixels representing a feature relevant to disease diagnosis;
wherein the first trained model comprises a convolutional neural network comprising a layer in which a first filter and a second filter are performed, at least one of the first filter and the second filter being a dilated convolution, wherein the output of the first filter and the second filter are combined and input into the subsequent layer.

According to another embodiment, there is provided a system for processing an image of tissue, comprising:
an input;
an output;
a processor configured to:
input received image data into a first trained model comprising a convolutional neural network, the first trained model generating a first set of output data representing a feature of the image relevant to disease diagnosis;
input the received image data into a second trained model comprising a convolutional neural network, the second trained model generating a second set of output data representing a feature of the image relevant to disease diagnosis;
combine the first set of output data and the second set of output data;
generate diagnostic information from the combined data using a third trained model.

The input may comprise a microscope and a digital imaging device configured to capture images of tissue through the microscope.

The methods are computer-implemented methods. Since some methods in accordance with embodiments can be implemented by software, some embodiments encompass computer code provided to a general purpose computer on any suitable carrier medium. The carrier medium can comprise any storage medium such as a floppy disk, a CD ROM, a magnetic device or a programmable memory device, or any transient medium such as any signal e.g. an electrical, optical or microwave signal. The carrier medium may comprise a non-transitory computer readable storage medium.

According to an embodiment, there is provided a carrier medium comprising computer readable code configured to cause a computer to perform any of the above methods.

FIG. 1(a) shows a schematic illustration of a system in accordance with an embodiment.

The system 1 comprises a processor 3 which takes input image data and generates an output. As will be described in more detail below, the output may be an image. Alternatively, the output may comprise diagnostic information, or a full diagnosis.

In an embodiment, the system comprises a graphical processing unit (GPU) and a general central processing unit (CPU). Various operations described in relation to the methods below are implemented by the GPU, whereas other operations are implemented by the CPU. For example, matrix operations may be performed by the GPU. For example, the image to image models, diagnosis models and various pre-processing operations comprising matrix or vector operations are performed by a GPU.

A computer program 5 is stored in non-volatile memory. The non-volatile memory is accessed by the processor and the stored code is retrieved and executed by the processor 3. The processor may comprise logic circuitry that responds to and processes the program instructions. The storage 7 stores data that is used by the program 5.

The system 1 further comprises an input module 11 and an output module 13. The input module 11 is connected to an input 15 for receiving the image data. The input 15 may be a receiver for receiving data from an external storage medium or through a communication network. Alternatively, the input 15 may comprise hardware such as image capturing apparatus. Alternatively, the input 15 may read data from a stored image file, which may be stored on the system or on a separate storage medium such as a floppy disk, a CD ROM, a magnetic device or a programmable memory device.

Connected to the output module 13 is output 17. The output 17 may comprise hardware, such as a visual display. Alternatively, the output may be a transmitter for transmitting data to an external storage medium or through a communication network. Alternatively, the output 17 may write data in a stored image file, which may be stored on the system or on a separate storage medium such as a floppy disk, a CD ROM, a magnetic device or a programmable memory device.

In an embodiment, the system 1 may be located in a common system with hardware for inputting and outputting data. Alternatively, the system 1 may be a remote system 1, which receives image data transmitted from a separate unit (for example an image capturing device), and transmits output data to another separate unit (for example a user computer comprising a screen). For example, the system may be implemented on a cloud computing system, which receives and transmits data. Although in the described system, a single processor 3 located in a device is used, the system may comprise two or more processors, which may be located in the same system or located remotely, being configured to perform different parts of the processing and transmit data between them.

In use, the system 1 receives image data through data input 15. The program 5, executed on processor 3, outputs data through the output 17 in the manner which will be described with reference to the following figures. The processor may comprise logic circuitry that responds to and processes the program instructions.

Where the system is integrated in a hospital or healthcare system, the system may also access information stored on the hospital or healthcare system, such as patient information or patient treatment history. Where the system is implemented as a web service (i.e. it is not integrated in a hospital/healthcare system) an image is uploaded and analysed. Other data such as patient information may be uploaded together with the image. The analysis output may be stored in a database and/or transmitted back to the user system. A hybrid approach can be implemented in which a histopathologist uploads a set of images and these are analysed within a hospital or healthcare integrated system.

Figure 1B:
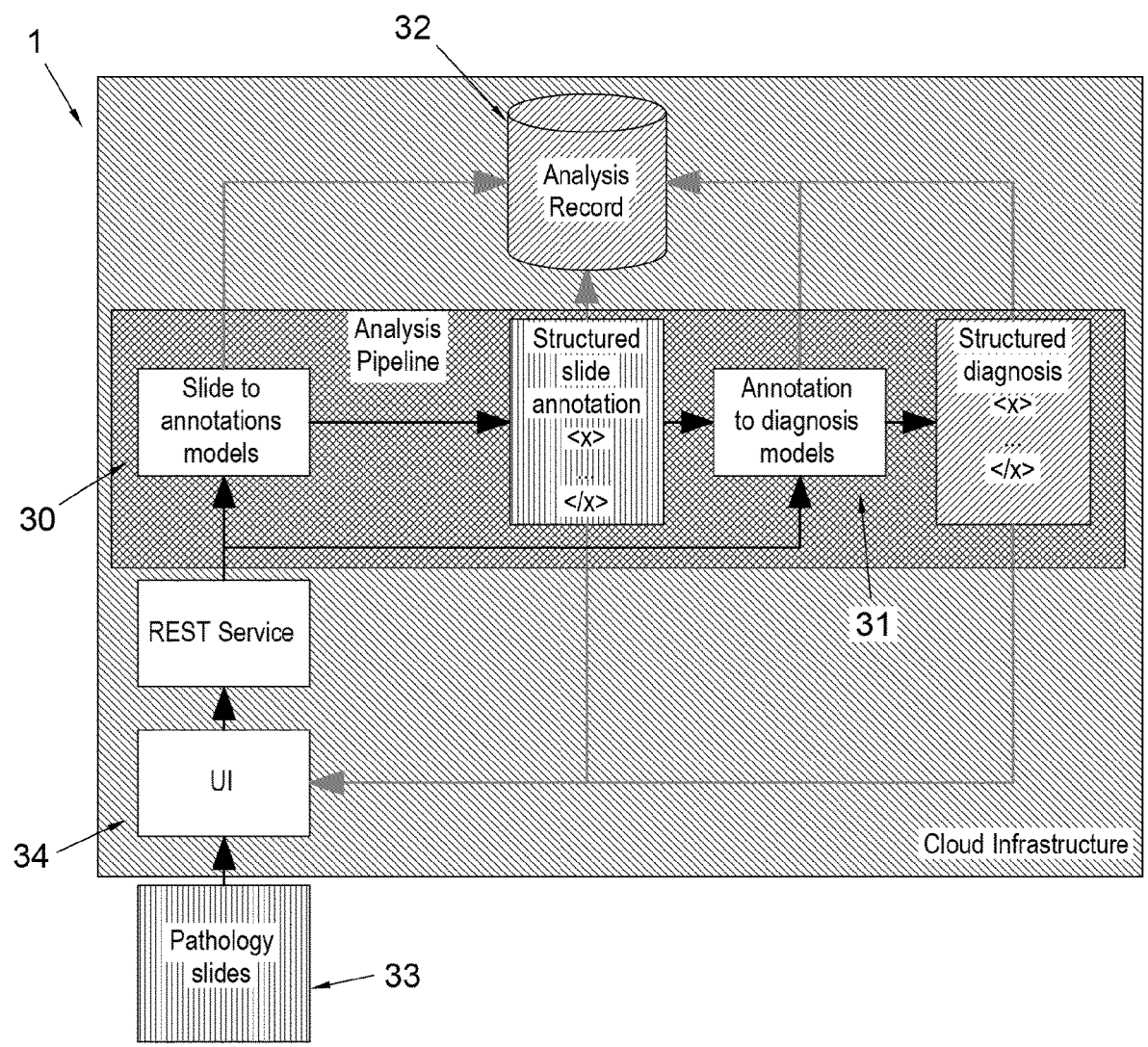
FIG. 1(b) is a schematic illustration of a system implementing a web-based service in accordance with an embodiment.

FIG. 1(b) is a schematic illustration of a system 1 implemented as a web-based service in accordance with an embodiment. The system 1 is implemented on cloud infrastructure.

The system 1 comprises a processor (not shown) which takes input image data and generates output data. Again, the system may comprise a GPU and a CPU. A computer program is stored in non-volatile memory in the cloud infrastructure. The computer program comprises one or more image to enhanced image models (also referred to as "slide to annotation models" 30 or "image to image annotation" models throughout the specification) and one or more diagnosis models (also referred to as "annotation to diagnosis" models 31 or "vector to vector diagnostic" models throughout the specification). Example image to image annotation models and diagnostic models will be described in detail in relation to the figures below. Although the term "image to image annotation" model is used throughout the description, it is understood that the output data from these models is not necessarily formatted as an "annotation" or an "image".

The input image data 33 is input through a user interface 34. A Representational State Transfer (REST) web service operates on the system. The REST service operates to re-construct pixel data from the transmitted data received from the user, and also manage transfer of data to and from the analysis record for example. These operations are performed on a CPU. The user interface 34 and REST service may also operate to receive user input selecting options for implementing the system, for example which models to use, which annotation information to display, which diagnostic information to output.

The output data from the annotation to diagnosis models 31, as well as the data output from the slide to annotation models 30, the data input to the annotation to diagnosis models 31, and a final output, is stored in cloud based storage, referred to as the analysis record 32.

The system 1 is implemented on a cloud computing system, which receives image data 33 and provides output data to cloud storage (referred to as the analysis record 32).

The system provides artificial intelligence-enabled automatic annotation and diagnostic technology for image-based diagnostics. In this example the system 1 provides cancer diagnosis based on an image of a histopathological slide, however other applications may be implemented.

Figure 2A:
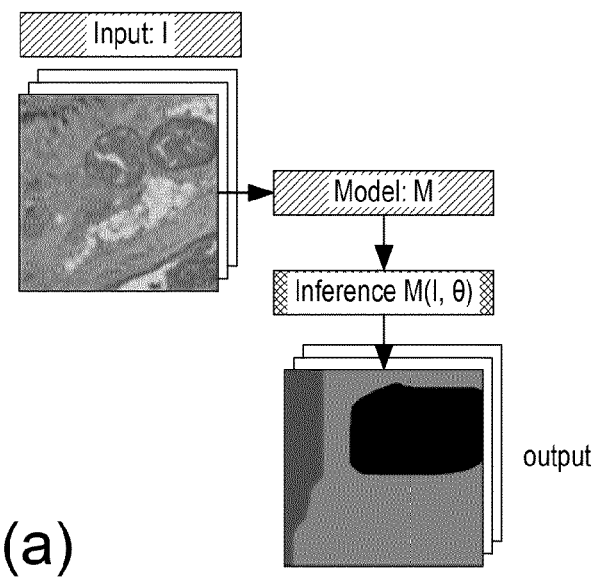
FIG. 2(a) is a schematic illustration of a method of image processing in accordance with an embodiment.

FIG. 2(a) is a schematic illustration of a method of processing an image of tissue in accordance with an embodiment.

Image data I comprising a plurality of pixels is input into a model M. The model M is an "image to image annotation" model. The model M is a trained model. A training process in accordance with an embodiment will be described below in relation to FIG. 3. The model is an image-to-image deep neural network based model.

The input image data I comprises pixel data. In the below description, the pixel data is red-green-blue (of dimension height×width×3), however the pixel data may alternatively be grayscale (of dimension height×width×1) for example. The input image data comprises a first number of pixels, where the first number is equal to height×width.

The image data may initially be acquired using a microscope mounted digital camera capturing images of tissue (also referred to as a histological section). The example input I shown in FIG. 2(a) comprises an image of a histological section stained with hematoxylin and eosin stain. However, various types of tissue images obtained using various methods may be processed using the described method.

The model M has a fixed input height and width. If an image is larger than the fixed input size, it is split into tiles having the fixed input size. The tiles may be contiguous or overlapping within the image. Each tile has a height and width corresponding to the fixed input size. In an embodiment, the input size is 512×512 pixels. An input image is first split into tiles of this dimension. Other input sizes may of course be used. For example, an input size corresponding to a power of 2 may be used, for example: 128×128, 256×256, 512×512, or 1024×1024 pixels.

In one arrangement, a whole slide image (WSI) scanner scans an entire tissue slice. The whole side image, comprising around 60 000 pixels height by 60 000 pixels width, is then split into contiguous tiles in an initial processing step. The tiles are then input into the model M one at a time.

The model M generates a value corresponding to each of a plurality of pixels representing a feature relevant to disease diagnosis. Classification is performed for each pixel of the input image, to segment the image into one or more categories which represent one or more features relevant to disease diagnosis. Examples of the kinds of classification categories that may be used include: one or more regions of interest within the image, coordinates of dividing cells, and segments of various tissues. Specific examples of categories will be described below in relation to FIG. 6. The model performs semantic image segmentation, meaning that each pixel in the input image is classified into one of a fixed set of categories. The number of categories is selected depending on the feature. There may be a single category, in which case the output of the model indicates whether the pixel corresponds to the category (1) or not (0).

The output of the model may also be referred to as an annotation or annotated image. The output has the same height and width as the input. For example, where the input data has a height of 512 pixels and a width of 512 pixels, the output is an array of values having height 512 and width 512. The values indicate the category. In the example output data of FIG. 2(a), there are three different categories (where in the example there are no regions corresponding to none of the categories). The different shaded regions of the output image correspond to the different categories.

The model M comprises a convolutional neural network (CNN). A CNN is a neural network comprising at least one convolutional layer. Pixel data can be directly input into a CNN. For example, no step of colour standardization, enhancement, noise reduction or filtering is performed prior to inputting the image data into the CNN.

In an embodiment, the first layer in the CNN is a convolutional layer. Each filter in the first layer has a depth matching the depth of the input data. For example, where the input data is RGB, the filter depth in the first layer is 3. The output volume of the first layer is determined by a number of factors, as follows.

The depth of the output volume of the layer corresponds to the number of filters. In an embodiment, there are 32 filters in the first layer, and therefore the output of the first layer has a depth of 32. The filters in the subsequent layer will therefore have a depth of 32.

The height and width of the output volume is determined by the height and width of the input, the receptive field size of the filters (both height and width) and the filter stride. When the stride is 1 then the filters slide one pixel at a time. When the stride is 2 then the filters slide 2 pixels at a time, producing a smaller output volume. Any zero padding used at the borders will also affect the output size.

During operation, also referred to as the forward pass, each filter is moved along the width and height of the input, taking a dot product at each position. The output values for one filter form a 2D array. The output arrays from all the filters in the layer are stacked along the depth dimension, and the resulting volume input into the next layer.

The model may comprise a plurality of convolutional layers, with various filters and numbers of filters, generating output volumes of various sizes. The filter weights are trainable parameters which are updated during the training stage, described below.

Figure 2B:
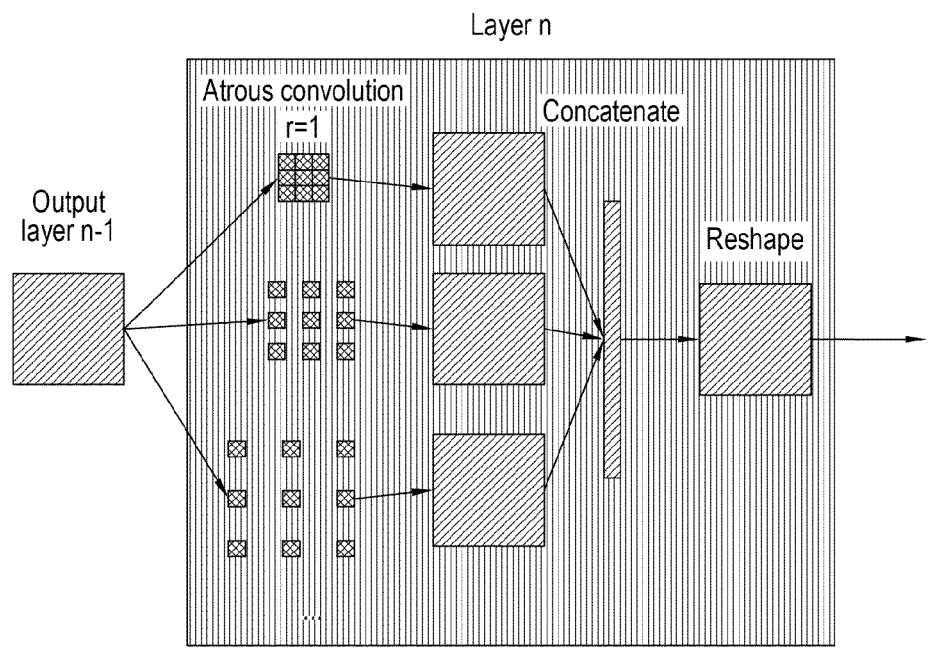
FIG. 2(b) is a schematic illustration of a convolutional layer used in a method of image processing in accordance with an embodiment.

As well as one or more standard convolutional layers, the convolutional neural network further comprises a hidden layer comprising a dilated convolution. This layer may be referred to as an Atrous convolution layer. FIG. 2(b) shows a schematic illustration of an example of such a layer, which is referred to in the figure as the nth layer, or layer n.

Figure 2C:
FIG. 2(c) is a schematic illustration of a dilated convolution operation.
Figure 2C:
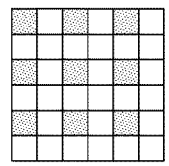

An Atrous convolution may also be referred to as a dilated convolution. A schematic illustration of a filter which performs a dilated convolution is shown in FIG. 2(c). The dilated convolution shown in FIG. 2(c) has a dilation factor of 2, and the filter has a receptive field size of 3×3. The dilated convolution operation (represented as *l) for a general unbounded case between an input I and a filter f with a dilation factor of l is:

$$(f *_l I)_t = \sum_{\tau=-\infty}^{\infty} f_\tau \cdot I_{t-l\tau}$$

The dilated convolution used in the convolutional neural network layer is bounded by the input size. Where the dilation factor is 1, the operation is the standard convolution operation as described above. Where the dilation factor is 2, as illustrated in FIG. 2(c), at each position the dot product of the filter values with input values spaced one apart is taken. The filter is moved along the width and height of the input according to the stride in the same way as before. However, the entries from the input are spaced apart by a distance determined by the dilation factor. Increasing the dilation factor thus broadens the effective receptive field for the filter without increasing the filter size, i.e. without increasing the number of parameters. Having a dilation factor of >1 means that non-local features can be learned, without increasing the number of parameters. Including a dilated convolution operation delivers a wider field of view without an increase in the number of parameters, and therefore computational cost. The receptive field can effectively be expanded without loss of resolution. Atrous convolution can also be defined as convolution of gapped sampling. By including convolutions with different dilation factors, both local and non-local features can be learned.

In the nth layer of the model M, multiple separate convolution operations are performed in parallel on the data taken as input to the layer. Each convolution operation is performed as a separate filter. At least one of the convolution operations is a dilated convolution. In an embodiment, two or more of the filters are dilated convolutions. One or more of the filters may have different dilation factors.

In the layer n shown, two of the convolution operations shown are dilated convolutions, having different dilation factors. The first convolution is a standard convolution having a first dilation factor being equal to 1, the second convolution is a dilated convolution having a second dilation factor being equal to 2, and the third convolution is a dilated convolution having a third dilation factor being equal to 3. However, various combinations may be implemented, and various numbers of filters may be included.

Each filter takes the same input (i.e. being the output data from the previous n−1 layer). Each filter therefore has the same depth as the output from the n−1 layer. Each filter has a different dilation factor. The layer may comprise a combination of Atrous convolutions with various dilation factors. The filters perform their operations in parallel, in the same manner as the filters in the standard convolution layers. Each filter outputs an array of values. The arrays may be of differing sizes.

The values from the output arrays are concatenated into a vector, which is then re-shaped to form a 2D array. This array is taken as input to the n+1 layer. The output of the filters is therefore combined and input into the subsequent layer.

Different convolution operations having different dilation factors are implemented in a single layer. By doing this, the layer is able to learn correlation of both local and non-local information at the same time, therefore allowing the learning of higher order spatial context. Information about both local and non-local features is propagated through the network. This is helpful for learning tissue morphology for example.

As well as convolutional layers, the model comprises one or more pooling layers. For example, pooling layers may be included to vary the spatial size. The pooling layers may be used to increase the width and/or height and decrease the depth of the output for example. The pooling layers may be "average pooling" layers. An average pooling layer comprises a filter having a spatial extent and stride, which is moved across the input, taking the average value at each position. Functions other than the average can be used however, for example, max pooling.

Up-sampling layers, for example one or more bilinear up-sampling layers may additionally or alternatively be included in order to increase the height and/or width of the output layer.

The model also comprises one or more activation layers. For example, the model may comprise one or more RELU (rectified linear unit) layers, which apply an elementwise activation function. A batch normalisation layer may be implemented after each convolutional layer. An activation layer may be implemented after a batch normalisation layer.

The model may comprise one or more units comprising a convolutional layer, a batch normalisation layer and an activation layer, or comprising a first convolutional layer, a first batch normalisation layer, a second convolutional layer, a second batch normalisation layer and an activation layer.

The model may further comprise one or more pixel-wise addition layers and/or concatenation layers. These layers act to combine the outputs from two or more previous layers.

One or more fully connected layers may be included after the convolutional layers. A dropout layer may also be included to mitigate overfitting.

A softmax is applied at the output. The softmax function is applied in a pixel-wise fashion. The softmax function takes as input the values for the pixel for all of the categories, and normalizes them into a probability distribution. Thus the softmax layer outputs, for a single pixel, a set of probability values corresponding to each category, the values being between 1 and 0.

The model may comprise a large number of layers. For example, the model may comprise over 100 layers.

The above description relates to an example illustration of a model M. In general however, different types of layers and different numbers and combinations of layers are possible in order to implement the model M for various use cases.

Optionally, the model M comprises a plurality of layers for which the output has a smaller dimension than the input. For example the height and/or width may be smaller than the input. In this manner, the height and width of the output may decrease through a number of the layers, whilst the depth increases. For example, there may be a first layer for which the output has a smaller height and/or width than the input, followed by one or more layers for which the output has the same dimension as the input, followed by a further layer for which the output has a smaller height and/or width than the input. For example, the first layer may take as input the image data (513×513×3) and output a volume (257×257×32). This layer applies a convolution using 32 filters, each of which outputs an array of volume 257×257. The height and width is reduced whereas the depth is increased. A batch normalisation and activation layer are then applied. The height and width can be reduced by adjustment of the filter hyper-parameters (e.g. stride) for example.

Figure 2D:
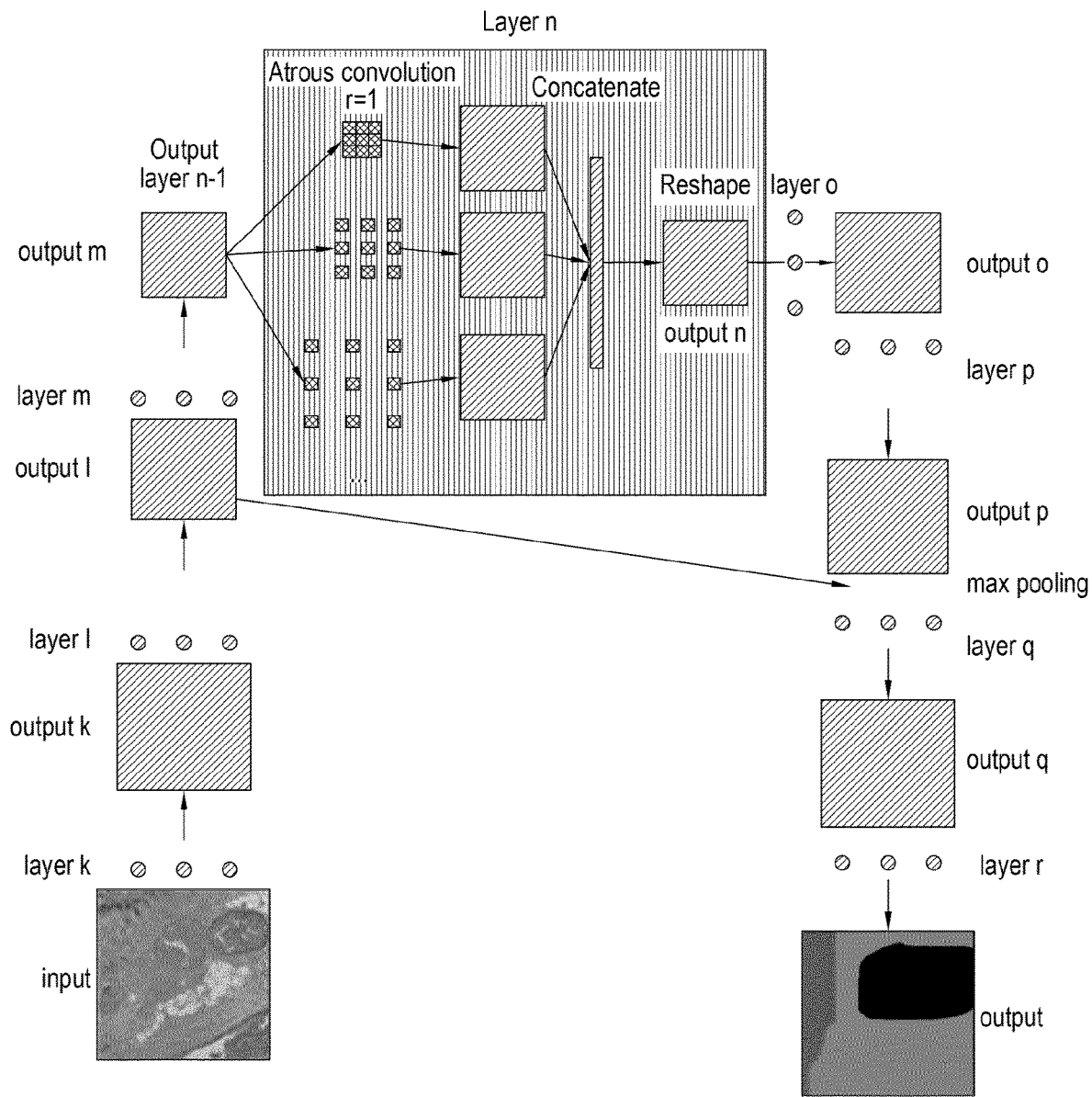
FIG. 2(d) is a schematic illustration of a convolutional neural network used in a method of image processing in accordance with an embodiment.

FIG. 2(d) shows a schematic illustration of a model architecture used in a method of image processing according to an embodiment, in which the height and width are reduced. Of course, in practice many more layers may be included, however the figure serves to illustrate how the spatial dimensions may be varied throughout the layers. Since the output of the model M has the same height and width as the input, the model M also includes at least one layer for which the output has a larger dimension than the input. The model M may have an "encoder/decoder" structure, whereby the layers first decrease the height and width, whilst increasing the depth (via the filter hyper-parameters such as stride size for example) and then increase the height and width whilst decreasing the depth (via pooling layers and/or bilinear up-sampling layers for example).

There is a single layer comprising one or more dilated convolutions. The layer comprising the dilated convolutions is located prior to the pooling and upsampling layers. The location of the layer comprising the dilated convolutions can be selected to be at various stages of the network depending on the use case. For example, by locating the layer comprising the dilated convolutions further through the network, higher level features can be learned in this layer.

In an embodiment, the layer comprises four filters, having dilation factors 1, 4, 8 and 12. However, various combinations of filters are possible. Although in the figure, the output of each filter is shown as having the same dimension, in practice each filter may have different output dimensions.

In an embodiment, the dilated filters have a stride of 1. In an embodiment, the dilated filters have the same receptive field size. In a further embodiment, the receptive field size is the same as the previous layer.

The model further comprises a skip connection. In practice, the model may comprise multiple skip connections, however for simplicity a small number of layers and a single skip connection is shown. A first layer m generates an output, referred to as output m, having a dimension smaller than the output of a previous layer. In this case, the output m is smaller than the output l and also smaller than the output k. Thus the output m is smaller than the output of the immediately previous layer l and is also smaller than the output of previous layer k.

A second layer q is subsequent to the first layer m. The input to the second layer q is generated from the input of the first layer m (also referred to as output l) as well as the output of the layer immediately prior to the second layer q (i.e. the output of the layer p). Inputting the output from the earlier layer directly to the later layer may be referred to as a "skip connection". The input of the first layer m is combined by pixel-wise addition with the output of the layer p. The result is then input into the second layer q. The skip connection may be implemented by including a pixel wise addition layer which combines the inputs.

If the skip connection is implemented by pixel-wise addition, the inputs must have the same dimension. In this case, the skip connection is implemented between layers having the same dimensions. For example, the first and second layer are selected such that the input of the first layer m is the same dimension as the output of the layer p (immediately prior to the second layer).

Using one or more skip connections, information from the downstream is fed directly to the upstream. This maintains high level global and regional visual features throughout the network. These are useful for large patch segmentation. Including the skip connections may be referred to as a "ladder" approach. In one or more of the layers, the output is smaller than the input. Inputting features from an earlier layer directly into a later layer, skipping one or more intervening layers, provides context.

The final layer generates an output having the same height and width as the input. The depth of the output is equal to the number of categories. Each output array along the depth corresponds to one output category. The values in each output array along the depth indicate whether the pixel corresponds to that category or not. A softmax function is applied to the values, to convert the values to probabilities. A probability of 1 indicates that the pixel corresponds to that category, a value of 0 indicates that the pixel does not correspond to that category. For each pixel, an argmax function is then applied, and the category corresponding to the highest value is selected as the category for the pixel. The argmax function may be applied by the CPU for example. Alternatively, the softmax function may be omitted, and an argmax function simply applied to the output values. By applying the softmax function first, probability information is also obtained.

By converting the selected categories to different values (0, 1, 2, and 3 for example) for each pixel, and superimposing the arrays, a single array having the same height and width as the input and indicating the category for each pixel may be generated. Each value can be converted to a different colour, in order to visually represent the annotations, as is shown in the figure. The output shown in the figure has three different categories. In an embodiment, there is a single category, indicating whether a particular feature is present for the pixel or not. In this case, no combining step is performed to generate the output. The probability values may be simply rounded to 1 or 0 and the resulting array output. In another embodiment, there are four output categories.

The output depth can be set by a convolutional layer having a number of filters corresponding to the desired output depth (i.e. desired number of categories). This convolutional layer may be located prior to the final layer, where the final layer is an up-sampling layer (for example using a transposed convolution) having the same output depth for example.

The output tiles are then joined to form a final annotated image, for example an annotated WSI. Optionally, a smoothing step may be performed on the resulting image, to smooth transitions between the tiles.

The model provides a quantitative assessment of a biopsy sample. For example, the model may be used in a method of diagnosing Ductal Carcinoma In Situ (DCIS). The model may be used to categorise nuclei cells. In this case there may be one category, indicating that the pixel corresponds to a cell nuclei. The segmentation output from the model allows measurement of the various nuclei cells, which delivers more granular insight, and in turn more accurate and explainable diagnosis.

Many measures of features relevant to diagnosis (such as Residual Cancer Burden (RCB) for example) can be determined through quantitative measurement of various physical aspects of the tissue sample. Such quantitative biomarkers require a quantitative assessment of a biopsy sample. The system provides automatic quantitative assessment. The system reduces image analysis time. For example, annotations may be produced within one and a half hours in some cases, even within 20 minutes in some cases.

Figure 3A:
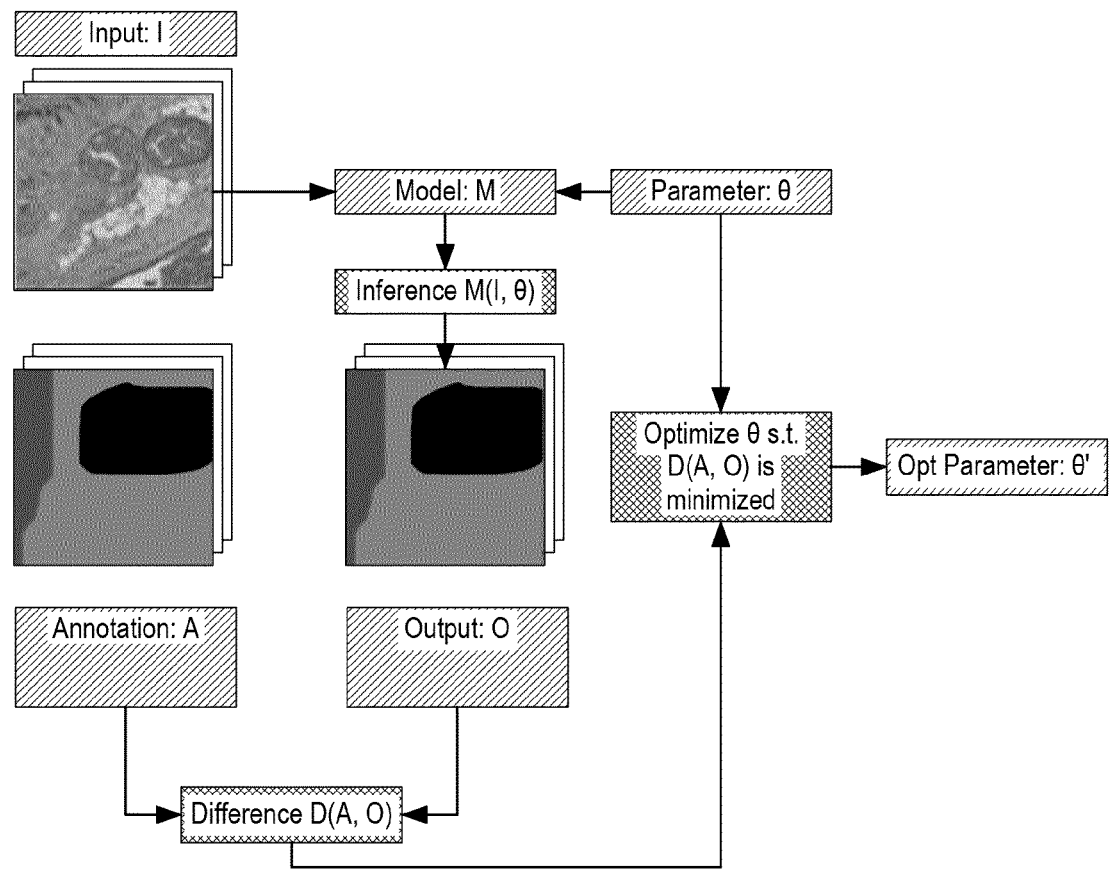
FIG. 3(a) is a schematic illustration of a method of training an image processing system in accordance with an embodiment.

FIG. 3(a) is a schematic illustration of a method of training a model M in accordance with an embodiment. The method trains the model to take input image data comprising a plurality of pixels and generate a value corresponding to each of the plurality of pixels, the values representing a feature relevant to disease diagnosis.

The input images are labelled I, the output from the model is labelled O, the annotations provided by a human expert are labelled A, and a difference measure, or loss, is signified as D. The model M has a parameter vector θ. The parameters include the filter weights for all of the convolutional layers. The model M takes input images to create inferred annotations O corresponding to M(I, θ). The goal of the training process is to find a parameter vector θ' so that the difference between the annotations and the inferred annotations is minimised, i.e.

$$\theta' := \operatorname{argmin}_\theta D(A, M(I, \theta))$$

M is the architecture of the network, while θ comprises the weights of the network. D represents a loss function. A pixel-wise cross entropy loss may be used, also referred to as the Categorical Cross Entropy. The pixel-wise loss is calculated as the log loss, summed over all possible categories C. This is repeated over all pixels and averaged to give the loss. The pixel-wise loss is defined for each pixel at coordinate (x, y) as:

$$D_{x,y}(A_1, A_2) = -\sum_{i}^{C} t_i \log(f_i(s))$$

where $t_i$ is the correct annotation of a pixel taken from the annotation A for the category, and $f_i(s)$ the softmax function for the i-th category (out of a total C categories). The value t is equal to 1 for the correct category and 0 for the other categories, for each pixel. The vector of $t_i$ values for each pixel may be generated automatically from the annotated image. For i-th category, $t_i$ indicates whether a pixel is annotated as the i-th category, where $t_i=1$ if the pixel is annotated as the category and 0 if not. The Softmax function $f_i(s)$ is given by:

$$f_i(s) = \frac{e^{S_i}}{\sum_{j}^{C} e^{S_j}}$$

where $S_j$ are the scores output by the final model layer for each category for the pixel. The loss then will be summed over every coordinate in the images.

Since there is no closed form for θ, the optimal parameters are computed by assigning random values as θ and then updating θ sequentially by computing the gradient of difference ∂D/∂θ and updating θ with the computed gradient. The gradient of the loss with respect to each of the trainable parameters of the model is determined through back-propagation. The gradients are then used to determine the updated parameters, using an optimiser function. This family of update methods is known as gradient descent (GGD), generally defined iteratively as:

$$\theta := \theta - \mu \frac{\partial D}{\partial \theta}$$

where μ is the learning rate defining how quickly the parameters are updated. The update may be performed based on a batch average. In an embodiment, a batch size of 8 tiles is used. In an alternative embodiment, a batch size of 16 tiles is used.

In an embodiment, an Adam optimization algorithm is used. The optimisation strategy selected may depend on the performance of each strategy on a use-case however. For example, one of the following optimisation methods may be selected:
Stochastic Gradient Descent (SGD)
AdaDelta
Adam
AdaMax
Nesterov Adam Optimiser
RMSProp The model is sensitive to pixel level annotations. In other words, if the training data were modified by just one pixel, parameters throughout the model may be updated differently. Including Atrous convolution filters of different sizes in a single layer in the model means that every pixel in the output is propagated from all around the input image. This means that a one-pixel difference can affect most parts of the neural network. This allows to update the model even with only one-pixel difference. Without using Atrous convolution, most changes may only be propagated locally.

Figure 3B:
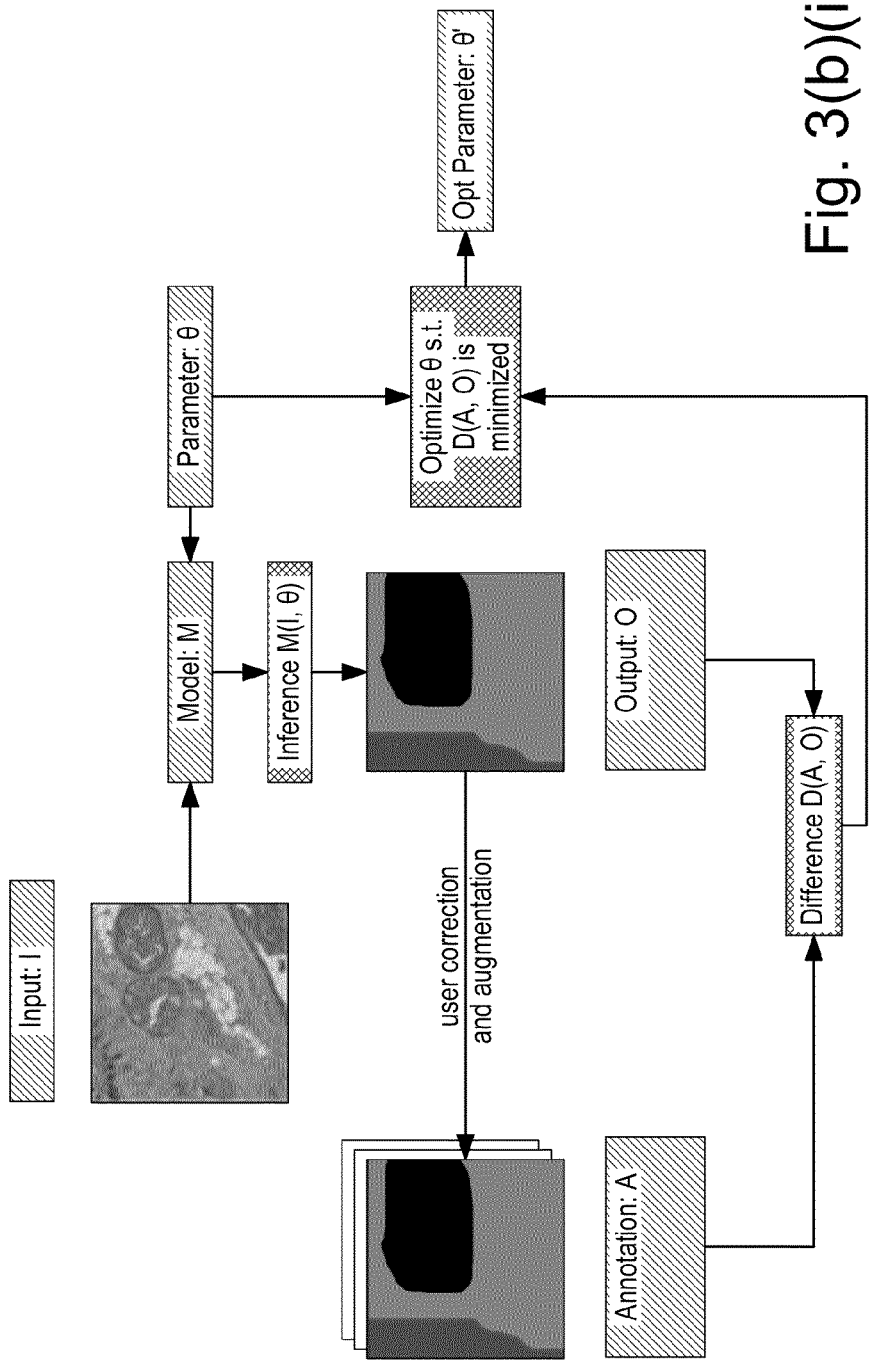
FIG. 3(b)(i) is a schematic illustration of an image processing method in accordance with an embodiment.

FIG. 3(b)(ii) is an illustration of a method of training an image to image annotation model that may be used in a training method in accordance with an embodiment. The figure shows the workflow of an example of pre-processing training data and training of an image to image annotation model. The figure shows how the input and correct training data is generated from a slide annotated by a human expert.

The model is trained using data extracted from images annotated by human experts in the above described manner. Various other methods of training may also be used, for example using alterative loss functions. Once trained, the model is then used to process images that were not seen in training. In use, images are processed through the model in a feed-forward manner, generating the output data.

Optionally, the model may be further updated in use, such that the parameters of the model are continuously refined even after the training stage is complete. FIG. 3(b)(i) is a schematic illustration of an image processing method in accordance with an embodiment, in which the model is further updated based on corrections to the output annotation made by a user. Modified data is generated by a user editing the output values via a graphical user interface. For example, the user may be presented with a visual representation of the image showing the regions identified as different categories output from the model. The user may edit the image to make modifications to the regions which are identified as corresponding to a particular category.

Tiles of the image are identified in which the output has been modified. The modified output and the original output for the tile are used to update the model parameters. The model parameters are adapted in the same manner as during the training stage, where the modified output is used to generate the correct pixel values (rather than these being taken from an image annotated from the basis image).

The model is able to detect correction by as little as one pixel. In other words, if the training data is corrected by just one pixel, parameters throughout the model may be updated. Including Atrous convolution in the model means that every pixel in the output is propagated from all around the input image. This means that a one-pixel difference will affect most parts of the neural network. This allows to update the model even with only one-pixel difference.

Without using Atrous convolution, most changes may only be propagated locally. This means that small pixel-level changes to the output do not necessarily trigger whole neural network-wide update. This potentially introduces local overfitting in an area where a correction happens. Furthermore, due to the non-local element of general convolutional layers, it is harder for the model to understand the difference as being caused by the underlying tissue feature.

Optionally, multiple training examples may be generated from the single modified image, in other words the modified data may be augmented. This increases the likelihood that the neural network updates even given the smallest change.

Figure 3C:
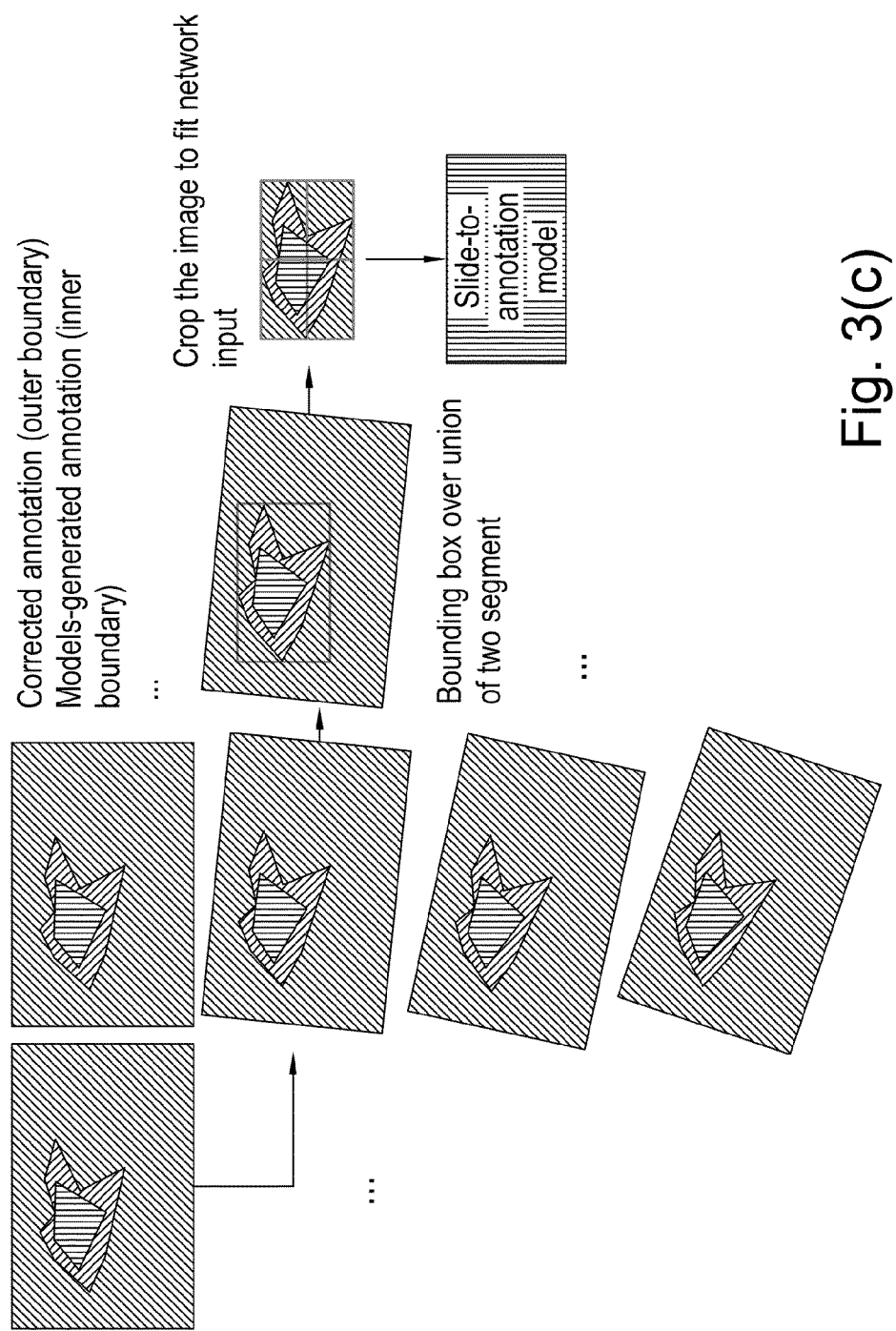
FIG. 3(c) shows a method of training data augmentation which may be used in an image processing method in accordance with an embodiment.

For example, the multiple examples may be created by rotating the image. FIG. 3(c) is a schematic illustration of a method of generating multiple training examples which can be used in an image processing method in accordance with an embodiment. A user can inspect and correct an output annotation. The corrected output annotation A' is then used to update the model in the following manner.

Given input I and expert-corrected annotation A', a first step is performed to augment the image by performing a rotation. In an embodiment, the rotation is performed by 5 degrees. This would result in 360/5=72 sample versions of the annotated image.

For every rotated image, a bounding box is created corresponding to the input size of the model M (e.g. 512× 512 pixels). The images are cropped into the appropriate input size of the network. The original input image is also rotated by the same amount, to generate multiple versions of the original input image. The corresponding tiles from the rotated input image are selected and inputted into the model M. The model is updated by training using the modified tiles, in the same manner as described previously. Slight corrections will directly update the weightings inside the image to image annotation model, ensuring that the model learns from an output error.

Figure 3D:
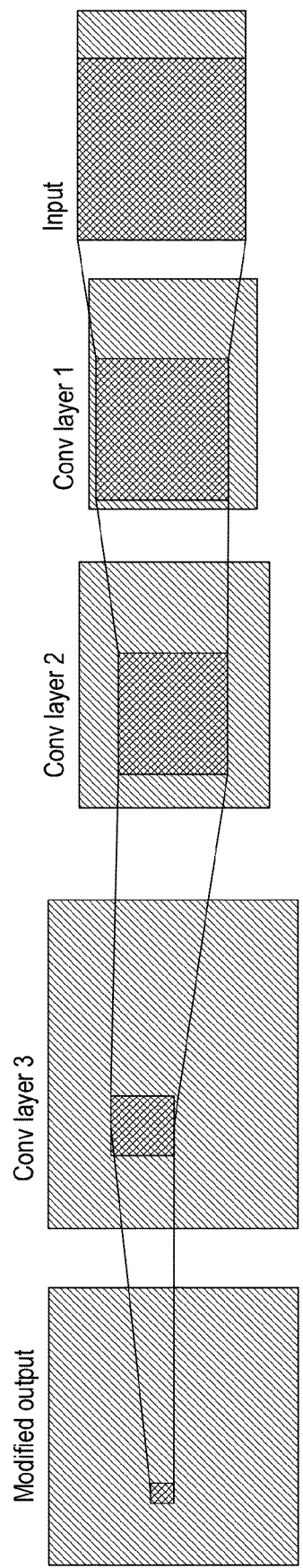
FIG. 3(d) shows a visualisation of the effect of a correction of one pixel in the output.

FIG. 3(d) is a schematic illustration showing the effect of modification of a single pixel in the output image. The model is shown with only three layers in order simplify the illustration, however in practice the model may have many more layers. The model M returns annotation information with the same dimension as the input image. The information for each pixel is continuously being passed inside the network. A small correction in output image of 1 pixel is initially propagated from a large area (potentially the whole image) of the input. Therefore, adjusting one pixel in the output means updating the weights to the area where the information for the pixel originates (shaded areas). The image-in-image-out approach maintains the information context throughout the network. This retention of information is used in the model update mechanism, meaning that even a change in one pixel will have impact throughout the network.

Combining data augmentation and image to image network architecture increases the likelihood that a small correction in annotation will impact the network during update.

Where the system is implemented by multiple users, updates to the model may be propagated to all users. For example, the image analysis system (IAS) sends an annotation modified by a user to a central system infrastructure, which may be hosted on the cloud for example. This triggers a model update sequence based on the corrected annotation. The updated model is then deployed to every IAS instance globally. FIG. 3(b)(iii) is a schematic illustration of an image processing system in accordance with an embodiment, in which a model update is performed on the cloud infrastructure, based on a correction made by one user. The updated model is then deployed to all users.

In this use case, the models are deployed alongside a locally-deployed or web-based Image Analysis System (IAS). Given input images, models are run producing annotations which are shown to users. Integration of deployed systems with a central infrastructure enables the deployed systems to be constantly improving after each use. By adding user interactions, the models continue to update by using annotation errors corrected by domain experts to update the model.

The output of the model M, comprising values corresponding to each pixel representing a feature relevant to disease diagnosis, may be presented directly to an expert user. The information may be presented in a visual representation through a graphical user interface. The expert user may then use the image information to make a diagnosis.

Figure 4A:
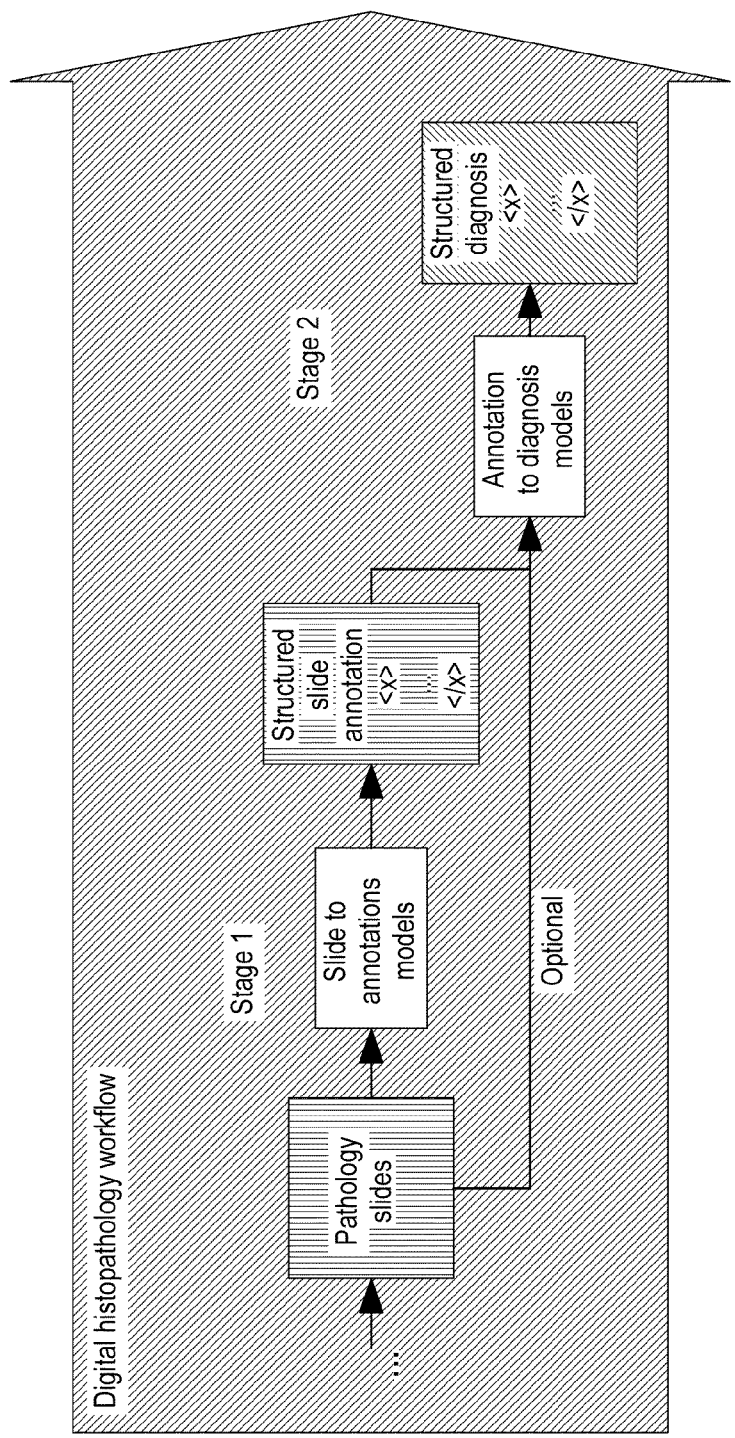
FIG. 4(a) is a schematic illustration of an image processing method in accordance with an embodiment.

Alternatively, the information output from the model is inputted into a further model, which generates diagnostic information. FIG. 4(a) is a schematic illustration of a computer implemented method of processing an image of tissue according to an embodiment, in which a further model generates diagnostic information. The method is divided into two stages.

The first stage comprises one or more models which receive image data as input, and generate values corresponding to each pixel representing a feature relevant to disease diagnosis as output, such as have been described previously. These models are based on deep convolutional neural network (DCNN) models. They output information relating to visual patterns such as: regions of interest (ROIs) within the image (e.g. regions corresponding to nuclei), regions of various type of cancer tissues (e.g. benign, in-situ, or metastatic), or regions of dividing cells.

Further processing is performed on the output of the image to image annotation model before it is input to the second stage.

In an embodiment, the output of the image to image annotation model is applied as a mask to the original image. Further information may then be extracted from the masked original image, for example the difference in colour distribution, size (e.g. number of pixels within the regions), shape and/or distribution of nuclei and/or chromatin of cancer cells, morphological characteristics of cancer tissues, density, or elongation and enlargement of cancer cells amongst others. This analysis can be performed on a masked whole slide image (WSI) scan of a histopathological sample. As described previously, the WSI is split into tiles, which are input into the image to image annotation model separately. The outputs for each tile are then combined, producing a single output from the first stage for the slide. Smoothing may be performed. This output is then applied as a mask to the original image and further information extracted from the original image. The first stage outputs this data to the second stage.

In an embodiment, further processing is performed to the output of the image to image annotation model to generate output data. For example, the outputs for each tile are combined, and the number of regions counted. The number is then input to the second stage as a scalar value. For example, where the first stage identifies regions corresponding to nuclei, the number of regions identified as nuclei are counted, and this number input to the second stage. Where the first stage identifies regions corresponding to dividing cells, the number of regions identified as corresponding to dividing cells is counted, and this number is input to the second stage. Alternatively, the number of pixels corresponding to the regions is counted. This number is then input to the second stage as a scalar value. For example, where the first stage identifies regions corresponding to tubule formation, the number of pixels corresponding to these regions is counted. This gives an indication of size.

Alternatively, the output data from the first stage is simply flattened into a vector, and inputted. Pre-processing pipelines are included to flatten the output arrays from the first stage into vectors and concatenate. These are realized as reduce-and-concatenate operands which convert image to vector.

Where more than one model is included in the first stage, each model outputs information relating to a different feature. For example, a first model may output information relating to distribution of nuclei, and a second model may output information relating to regions of interest. This information is combined before being input to the second stage.

The model or models in the first stage may be referred to as "image to image annotation" models. Each image to image annotation model takes visual information as input and outputs data representing a feature of the image relevant to disease diagnosis. The output data can also be referred to as annotations. The feature may be: regions of interest within the image, regions of dividing cells, or regions of various tissues for example. Each feature is implemented as a separate model, for example, inferring regions of interest within the image is implemented as a single model, detecting coordinates of dividing cells is implemented as a single model etc. Further processing is performed on the output data, before it is input to the second stage.

The second stage comprises one or more further models, referred to as diagnosis models. These models may be based on classification methods or regression methods, for example deep neural network based methods. They take as input the data output from the first stage, and output diagnostic information. Optionally, the second stage may also take as input non-visual aspects of diagnosis such as patient information.

As described above, some pre-processing is performed on the values output from the first stage before inputting to the second stage. For example, the pre-processing comprises reduction of the output matrix into vector form. Where multiple models are included in the first stage, the output from each is converted into a vector or a scalar as described previously. The outputs are then combined into a vector (for example the vectors are concatenated into a larger vector), which is taken as input to the second stage model. Where multiple models are included in the second stage, the vector may be input into each model. Alternatively, different combinations of features from models in the first stage may be input into each model in the second stage. The models in the second stage may be referred to as "annotation-to-diagnostic" models or vector to vector diagnostic models. Although the term "vector to vector" model is used, the model may output a scalar value. The model or models in the second stage may be implemented as deep neural networks which take an input vector and pass the values across the hidden layers to produce diagnostic information as output. The output diagnostic information may be encoded as a vector or a scalar.

As described above, the pre-processing may comprise generating further information from the output of each image to image annotation model. This may comprise applying the output as a mask to the original image, and generating information such as an indication of a difference in colour distribution, an indication of size, shape and/or distribution of nuclei and/or chromatin of cancer cells, an indication of morphological characteristics of cancer tissues, an indication of density of regions, or of elongation and enlargement of cancer cells from the masked image.

For example, where the image to image annotation model indicates regions of cancer tissue, this output is applied to the original image as a mask. The mask output comprises the pixel information for the pixels corresponding to the cancer tissue only. This pixel data is then analysed to produce a vector of values representing a colour difference. For each RGB array, the number of pixels corresponding to each pixel value (for example the values 0 to 255) is determined. These are formed into a vector. Alternatively, and as described above, the pre-processing may comprise counting the number of detected regions or the number of pixels in detected regions for example.

A diagnostic model in the second stage comprises a neural network. Data output from the first stage is taken as input to the neural network. The neural network comprises a plurality of layers. The hidden layer or layers comprise at least two nodes. Each node in the input layer computes a weighted sum of all of the input values (and optionally an additive bias term) and then applies an activation function to the result. The outputs of each layer are then fed as the inputs to the next layer. Each node in the hidden layer again computes a weighted sum of all of its inputs (being the outputs of each node in the previous layer), and then applies an activation function to the result. Each node in the final layer outputs a value. The weights and biases are the trainable parameters, the values of which are learned during the training stage (described later).

The neural network may be a classifier type neural network, which outputs a probability value for each of a plurality of categories. For example each category may correspond to a grading (e.g. low, medium, high). Alternatively, the neural network is implemented as a regression type neural network, and outputs a scalar value. The diagnosis model in this case outputs a scalar. For example, the output may be a value corresponding to the mitotic cell index.

In an embodiment, the input image information is also taken as part of the combined input into the second stage.

In an embodiment, the neural network has an input size is smaller than the size of the vector output from the first stage. The neural network is then implemented repeatedly, sliding along the vector output from the first stage. The output of each implementation is then summed to give a final output from the second stage.

Alternatively, the neural network has an input size corresponding to the size of the vector output from the first stage, and is implemented once for each input image.

The method comprises a first stage, in which one or more models receive input image data and output information labelling pixels of the image according to features relevant to disease diagnosis. The method further comprises a second stage, in which one or more models receive input information generated from the pixel labels and output diagnostic information. By splitting the method into two stages, comprising separate models, the output diagnostic information is explainable. An expert user can refer to the image labels to check the validity of the output diagnostic information.

Including multiple models in the first stage, which feed separately into the second stage, provides a multi-context analysis pipeline. The term "context" here is used to refer to the visual image information output from the different models in the first stage. By feeding the information from two or more models into the second stage separately, i.e. in parallel, error propagation is mitigated.

Given a WSI, various models (referred to as image to image annotation models) are applied to the image, in a multi-model approach. Every model will output an annotation which will then be passed on the next model or set of models (diagnostic model or models). The next set of models then take this output and infer high-level diagnosis information. The results from stage 1 and 2 can then be shown to the user (who may be a histopathologist) who may either approve or modify the result. If the result is modified, further steps may be performed in a similar manner as has been described in relation to the image to image annotation models, in order to update the diagnosis model parameters based on the correction.

Image to image annotation models are trained taking the WSI as input, and the corresponding visual annotations made by human experts, used to generate the labels. Diagnostic models on the other hand are trained on visual and textual annotations as input and corresponding diagnostic information as labels. The models are trained separately.

Figure 4B:
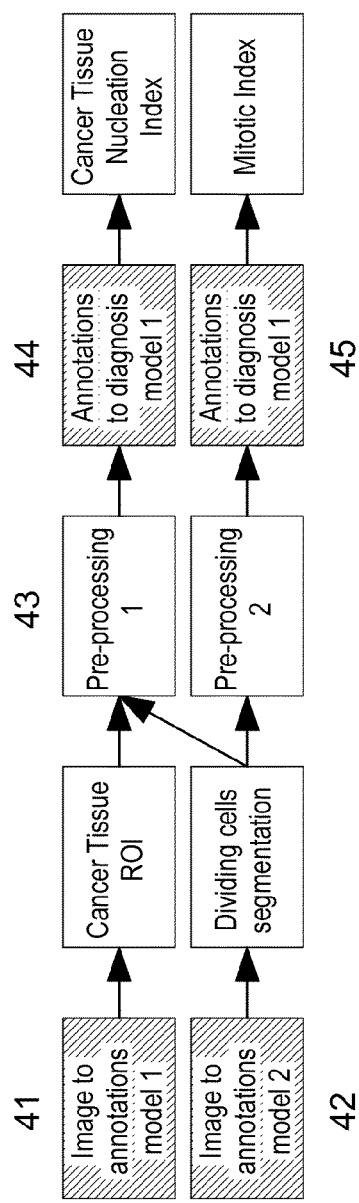
FIG. 4(b) is a schematic illustration of an image processing method in accordance with an embodiment.

FIG. 4(b) shows a schematic illustration of a method in accordance with an embodiment, in which two models are used in the first stage, and two models are used in the second stage. The method is used to generate diagnostic information used to diagnose cancer. In the first stage, a first model 41 labels the pixels in the image in order to indicate cancer tissue regions of interest. A second model 42 labels the pixels in the image in order to indicate dividing cells. The output from the first model and the second model is combined, generating an output indicating the regions corresponding to dividing cells within the cancer tissue regions of interest. A Hadamard product may be used to combine the output. Information from the combined image (for example the number of regions) is then input into the third diagnosis model 44. The number of regions can be determined using an object counting algorithm for example. The output from the second model is input to the pre-processing stage 2. Information such as the number of dividing cells (i.e. the number of regions) is then input into the fourth diagnosis model 45.

The third model 44 outputs diagnostic information. In this case, the diagnostic information is a cancer tissue nucleation index value. The diagnosis model in this case is implemented as a regression model, which outputs a value. Alternatively, it may be implemented as a classification model, where the categories correspond to e.g. 0-10%, 11-20%, etc. The fourth model 45 outputs diagnostic information. The diagnostic information in this case is a mitotic index value. Again, the diagnostic model may be implemented as a regression model or a classification model.

One use case may use some annotation types as the input while another use case might use another set of annotation types. FIG. 4(b) shows an example of two annotation-to-diagnostic models taking two different sets of annotations as input.

The diagnostic information output from the models in the second stage does not have to be a final diagnosis. For example, diagnostic information such as: cancer tissue nucleation index, mitotic index, a grading, tumour size, a metastatic index, or a nodal index may be output.

Figure 4C:
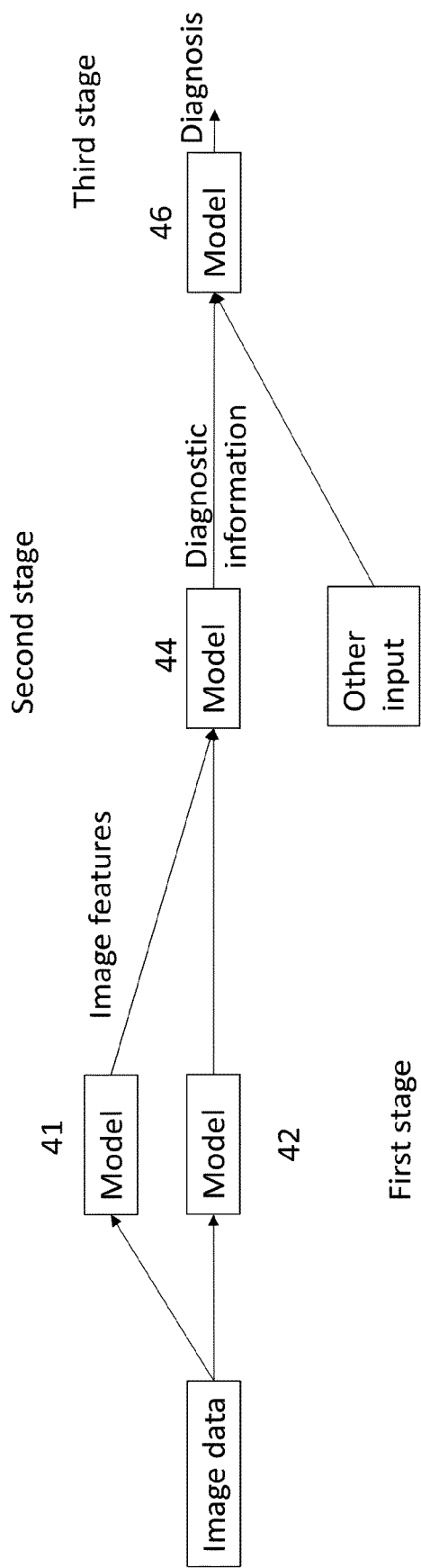
FIG. 4(c) is a schematic illustration of a method of diagnosis in accordance with an embodiment.

FIG. 4(c) is a schematic illustration of a method of disease diagnosis in accordance with an embodiment. The method comprises multiple image-to-annotation models followed by an intermediate diagnostic model, and then a final diagnosis model.

As has been described previously, image data is inputted into one or more models (in the example shown a first model 41 and a second model 42) in the first stage. Each model in the first stage labels the pixels in the image in order to indicate a feature relevant to disease diagnosis. The different models are directed to different visual features. The outputs from the one or more models in the first stage are combined and used to generate input into one or more models in the second stage (in this case a third model 44) which generates diagnostic information. The diagnostic information output from the third model 44 in the second stage is a value representing diagnostic information, for example a cancer tissue nucleation index or a mitotic index. The output from each model in the second stage is combined.

Optionally, further information from other sources is also combined with the information output from the second stage. For example, contextual information such as patient gender, patient age and other information may be included. This information is converted to categorical values or encoded into numerical values, and combined with the numerical output from the second stage.

The combined information is then input into a final diagnosis model 46 in a third stage. The output from this model may be a binary output, indicating whether cancer is detected. Alternatively, there may be multiple categories corresponding to different types of cancer, for example different types of breast cancer. The final diagnosis model 46 may again comprise a neural network comprising a plurality of layers. The hidden layer or layers comprise at least two nodes. Each node in the input layer computes a weighted sum of all of the input values (and optionally an additive bias term) and then applies an activation function to the result. The outputs of each layer are then fed as the inputs to the next layer. Each node in the hidden layer again computes a weighted sum of all of its inputs (being the outputs of each node in the previous layer), and then applies an activation function to the result. Each node in the final layer outputs a value. The weights and biases are the trainable parameters, the values of which are learned during the training stage (described later). The neural network may be a classifier type neural network or a regression type neural network.

The output of the annotations-to-diagnosis stage is diagnostic information. This diagnostic information is then fed into a final diagnosis model 46 which outputs a final diagnosis of a disease. In some cases, several layers of annotation-to-diagnoses are used.

Figure 5:
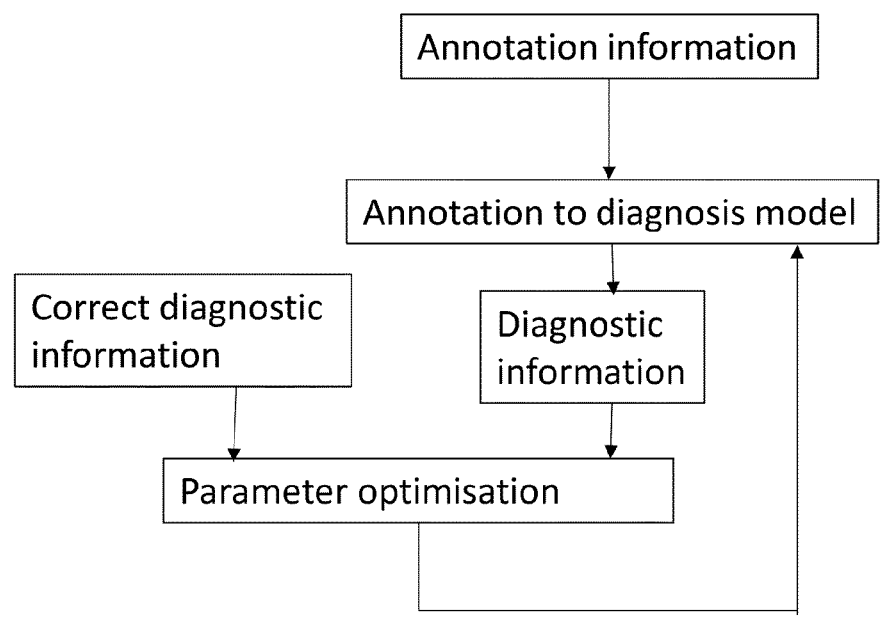
FIG. 5 is a schematic illustration of a method of training a diagnosis model used in a system in accordance with an embodiment.

FIG. 5 is an illustration of a method of training a diagnostic model comprising a neural network, that may be used in a training method in accordance with an embodiment. The diagnosis model is implemented as a vector-to-vector deep neural network model.

As described during operation, input information generated from pixel labels is input to the model. The pixel labels may be generated by a human expert, manually labelling a tissue image. As during operation, each node computes a weighted sum of all of its inputs, and optionally an additive bias term, and then applies the activation function to the result. The results pass through the network in the same manner as during operation, and the network outputs diagnostic information.

The human expert also generates diagnostic information based on the image. For example, the human expert labels the image with the diagnostic information such as a cancer tissue nucleation index or a mitotic index, or a grading. This information is then used as the correct diagnostic information labels during training. For example, the human expert labels the mitotic index, and the model is then trained to output the correct mitotic index.

Where non-visual annotations are included in the input to the diagnosis model, the values are converted to categorical values during pre-processing where applicable. In this case, the same Softmax and distance functions described previously are used.

In case that any annotations cannot be encoded into a categorical value, those annotations are encoded into a numerical value. The distance functions used in this case may be either L1 or L2 distance, defined as:

$$D(A_1, A_2) = \sum_i |A_{1i} - A_{2i}|$$

and $$D(A_1, A_2) = \sqrt{\sum_i (A_{1i} - A_{2i})^2}$$

respectively.

For each input, the gradient of the loss with respect to each of the trainable parameters of the neural network (i.e. the weights and biases) can be determined through back-propagation, and used to update the parameters. The data may be inputted in batches, and the update performed for each batch. Every operation performed in the forward pass is differentiable and therefore a functional expression for the derivative of the loss with respect to each parameter can be determined by the chain rule. The gradient values are calculated from these expressions using the back-propagated error and the activations (inputs for each layer from the forward pass, cached during the forward pass). This results in an array of gradient values, each corresponding to a parameter, for each input in the batch. These are converted to a single gradient value for each parameter (for example by taking the average of the gradient values for all tasks for the particular parameter in the batch).

The resulting gradient for each parameter is then used to calculate the updated parameter from the previous values using an optimizer function (e.g. a gradient descent type optimiser function). The input to the optimiser function for each parameter is the previous value, the corresponding gradient value and a learning rate parameter. In general, gradient descent based optimizers update the parameter in the direction of steepest descent of the loss function with respect to the parameter, scaled by a learning rate. The parameters are replaced with the new values and the process iterates with another batch of training examples.

The annotation-to-diagnostic model does not take the visual input directly. Rather, the models take descriptive information of the images encoded as visual, and optionally textual, annotations. Those annotations are first pre-processed into numerical or categorical values. All the annotation values then are combined into one input vector to the model.

Figure 6A:
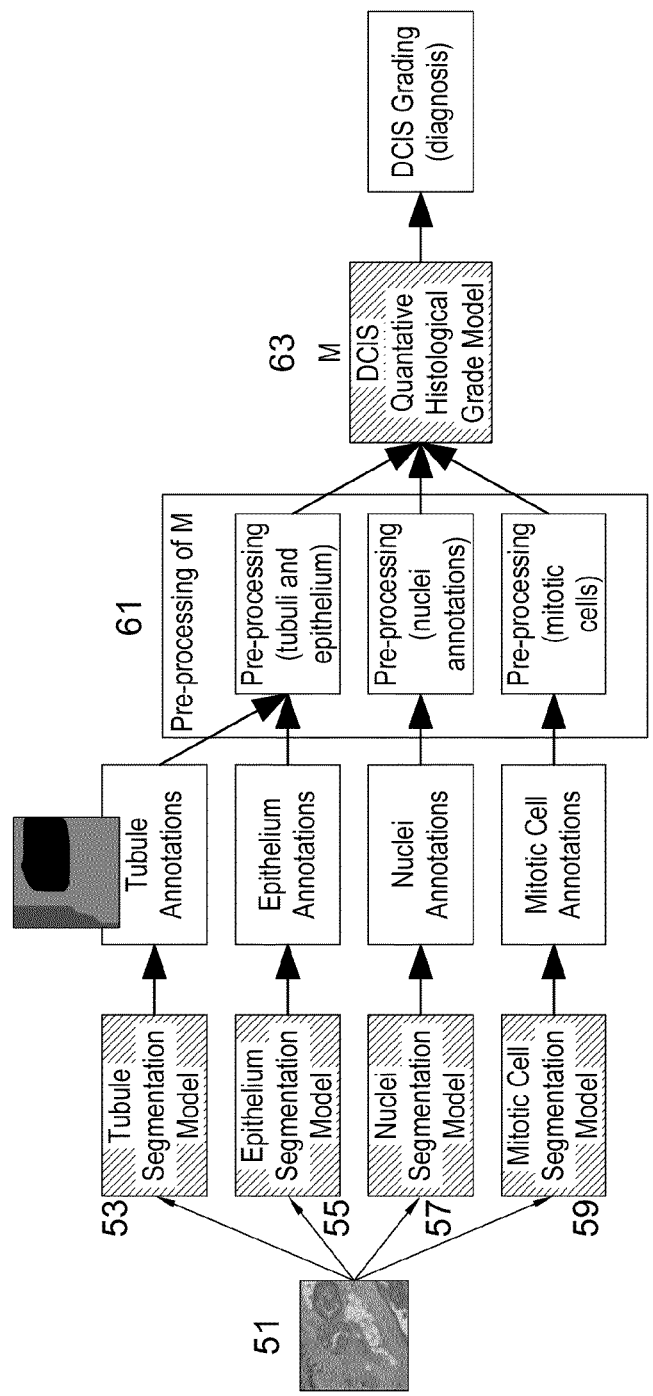
FIG. 6(a) is a schematic illustration of a method of image processing in accordance with an embodiment.

FIG. 6(a) shows a schematic illustration of a computer implemented method of processing an image of tissue according to an embodiment. The method is directed to diagnosis of Ductal Carcinoma In Situ (DCIS). However, although a specific application is shown in order to illustrate the method, various other diseases may be diagnosed using various combinations of image processing models.

The input image data comprises pixel data as has been described previously. The pixel data in this example is red-green-blue (RGB) pixel data, however the input may alternatively be grayscale. The image data is acquired using a microscope mounted digital camera capturing images of a slice of breast tissue (also referred to as a histological section). The histological section is stained with hematoxylin and eosin stain, and the image taken of the stained section. A whole slide image scanner scans the entire tissue slice. The WSI is split into tiles having a height and width corresponding to the input height and width size of each of the models 53-59. In an embodiment, the input size is 512×512 pixels. Each model may have a different input size.

Figure 6B:
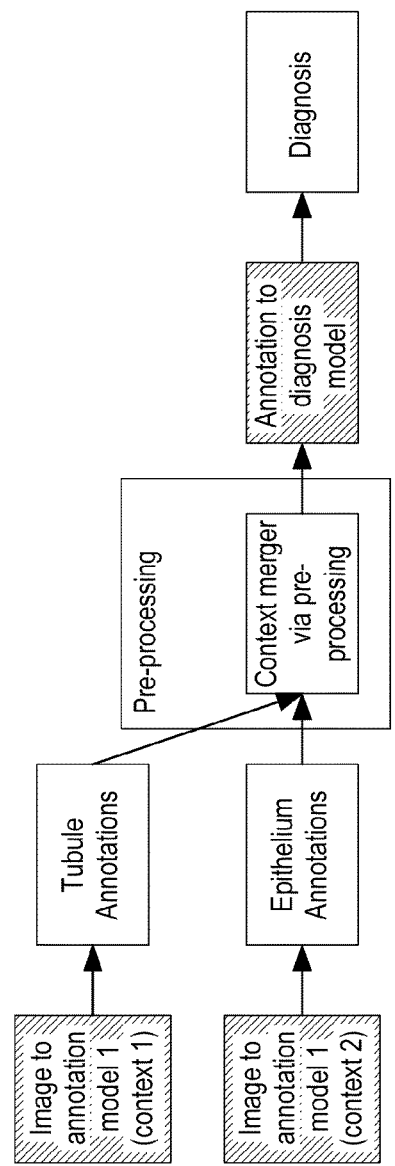
FIG. 6(b) is a schematic illustration of a method of image processing in accordance with an embodiment.

The image data 51 is inputted into a plurality of trained models 53-59 in a first stage. In the method shown in FIG. 6(a), there are four trained models 53-59 in the first stage, however a different number of trained models may be used. For example, FIG. 6(b) shows a method in which two trained models are used in the first stage. In this case, only the tubule segmentation model 53 and epithelium segmentation model 55 are used.

A first trained model is a tubule segmentation model 53, the second trained model is a epithelium segmentation model 55, the third trained model is a nuclei segmentation mode 57, and the fourth trained model is a mitotic cell segmentation model 59. Each of the tube formation in the sample, the differentiation of epithelial cells to carcinoma, the visible nuclei in the sample and the number of dividing cells is used to diagnose DCIS in this method.

Each trained model comprises a convolutional neural network. Each model takes as input image data, i.e. pixel values. Each trained model outputs a value corresponding to each pixel in the manner that has been described previously.

The tubule formation model 53 generates a value corresponding to each pixel indicating whether the pixel corresponds to a region of the image in which the cells are in tubule formation. The model uses a single category. In this manner it detects the segments within the image which contain tubule formation.

The epithelium segmentation model 55 provides information relating to the differentiation of epithelial cells to carcinoma. The epithelium segmentation model 55 generates a value corresponding to each pixel indicating whether the pixel corresponds to a region of the image which corresponds to an epithelial cell. In this manner, it detects segments within the image containing various stages of epithelial segmentations. The model uses a single category.

The nuclei segmentation model provides information relating to the visible nuclei in the sample. The nuclei segmentation model 57 generates a value corresponding to each pixel indicating whether the pixel corresponds to a region of the image which corresponds to a cell nucleus. In this manner, it detects the segments within the image containing a nucleus. The model uses a single category.

The mitotic cell segmentation model provides information relating to the number of dividing cells. The mitotic cell segmentation model 59 generates a value corresponding to each pixel indicating whether the pixel corresponds to a region of the image which corresponds to a mitotic cell. In this manner, it detects the segments within the image containing cells that are dividing. The model uses a single category.

Each model generates a value corresponding to each pixel, since in this case there is a single category. A softmax function is applied to convert the value into a probability. Thus for each model, a value is generated for each pixel indicating whether the feature (e.g. dividing cell) is present (1) or not (0). These probabilities are then converted to values, i.e. 1 or 0, by applying a rounding function.

The outputs for each tile in the image are then combined to form an output corresponding to the original input size. A smoothing function may be applied at this stage. The output of each trained model thus comprises a 2D array of the same height and width as the original input, also referred to as a set of output data. For each model, the values represent a feature relevant to disease diagnosis (e.g. tubule formation).

At stage 61, pre-processing is performed. The mitotic cell segmentation model 59 outputs an array of 0 and 1 values, with 1 indicating the pixel is in a region of the image corresponding to a mitotic cell. The number of mitotic cell regions is counted by applying a function during the pre-processing stage 61. Any suitable object counting algorithm can be used. For example, a depth-first search (DFS) algorithm may be used. This function may be performed on the GPU.

The nuclei segmentation model 57 outputs an array of 0 and 1 values, with 1 indicating the pixel is in a region of the image corresponding to a nuclei. The number of nuclei regions is counted by applying a function during the pre-processing stage. Again, any suitable object counting algorithm can be implemented on the GPU.

The epithelial cell segmentation model outputs an array of 0 and 1 values, with 1 indicating the pixel is in a region of the image corresponding to a epithelial cell. The tubule segmentation model outputs an array of 0 and 1 values, with 1 indicating the pixel is in a region of the image corresponding to a tubule. The outputs are combined by a Hadamard product operation, which may be performed on the GPU. The result is a matrix of values, with 1 indicating the pixel is in a region of the image corresponding to an epithelial cell in a tubule formation, and 0 indicating that it is not. The number of pixels having a value of 1 is then counted, and this is taken as output.

A vector comprising this value, the number of nuclei regions and the number of mitotic cell regions is formed and output from the pre-processing stage 61. Other information may also be included in the vector, for example a value representing patient information (age, gender).

Although in this example, the output from each model is processed into a scalar number, in an alternative embodiment, the set of output data from each of the models is combined to form a single vector of input data. A flattening function is applied to each matrix, and the resulting vectors concatenated to form a combined data set. This pre-processing comprises reduction of the matrix output from each model into vector form, concatenation of the vectors into a larger combined vector and passing the combined vector as input to the DCIS quantitative histological grade model 63.

In this method, a single "diagnostic" model, the DCIS quantitative histological grade model 63, is included. However, as has been described previously, where multiple "diagnostic" models are included, different combinations of data may be fed into each.

Diagnostic information is then generated from the combined data using the DCIS quantitative histological grade model 63. The diagnostic information output is a DCIS grading. In this case, the model 63 is a classification type model, with each output category corresponding to a grading (for example none, low, intermediate, high). A softmax is applied as the final layer, such that the value output for each category indicates the probability that the grading is the corresponding category. The DCIS quantitative histological grade model 63 is an annotation-to-diagnostic model. This model may comprise a deep neural network which takes the input vector corresponding to the combined data and passes the value across the hidden layers to produce diagnosis information, which is encoded a vector. The output may be converted to a single value, for example an argmax function is applied to select the category with the highest probability, and this is output as the grading (e.g. intermediate).

Each model is trained separately to the others. In particular, the tubule segmentation model 53, epithelium segmentation mode 55, nuclei segmentation model 57 and mitotic cell segmentation model 59 are trained separately from each other. The training data for each of these models may be extracted from the same annotated images however. For example, each image in a training set of images may be annotated with the tubule regions, the epithelium regions, the nuclei regions and the mitotic cell regions by a human expert. The annotated images are split into tiles corresponding to the input size. From each image, four sets of training data are generated, one for training each model. For example, for the tubule segmentation module, a function is applied to the annotated image extracting a 2D array of 1 and 0 values, one value for each pixel, with 1 indicating the pixel corresponds to a tubule and 0 indicated that it does not. This is done for each feature, resulting in a 2D array for each model. Thus training data for each model may be automatically generated from a single image which has been annotated by an expert.

The annotation data may be in the format of a tensor of coordinates, indicating pixels identifying the boundaries of the regions corresponding to each feature. The tensors for each feature are then used to generate an array of training data, by populating the bounded regions with 1 entries, and populating the remaining regions with 0 entries for example. This may be implemented using a fill operation for example.

The DCIS quantitative histological grade model 63 is also trained separately to the other models. During training, the input to DCIS quantitative histological grade model 63 is generated directly from the image annotated by the human expert. Each annotated image is also assigned the diagnostic information by the human expect. The diagnostic information assigned by the human expert is used to train the DCIS quantitative histological grade model 63, in the manner described previously.

Figure 7:
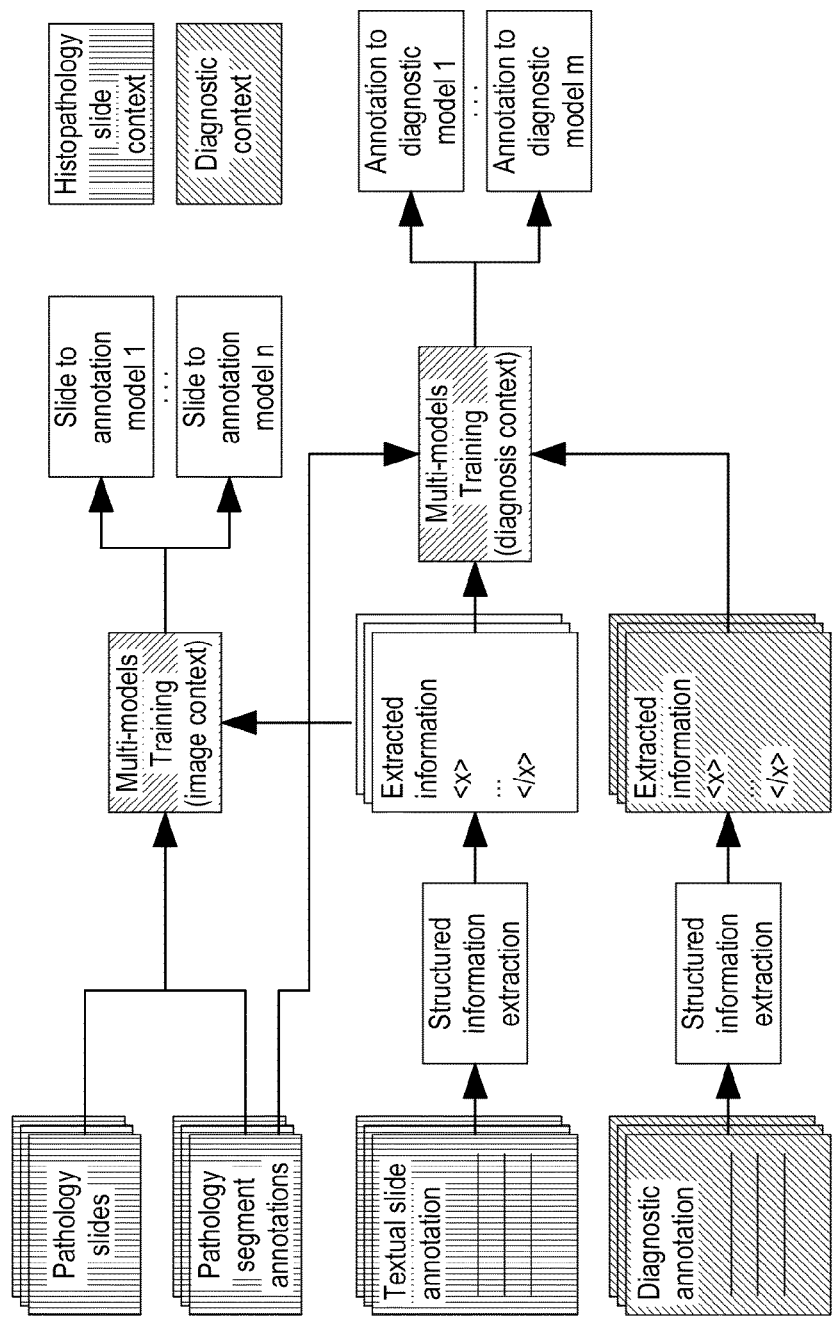
FIG. 7 is a schematic illustration of a method of training an image processing system in accordance with an embodiment.

FIG. 7 shows a method of training in accordance with an embodiment. Data comprising the image data (pathology slides), the annotated image data (pathology segment annotations indicating e.g. tubule regions, epithelial cell regions, nuclei regions and mitotic cell regions), any textual slide information (e.g. patient age, gender), and the diagnostic information (e.g. the grading) is taken as input. The image data is used as the model input for the stage 1 models. The annotated image data is processed to generate the correct training labels for the stage 1 models. The annotated image data and optionally any textual information is used to generate the input for the stage 2 models. The diagnostic annotation is used to generate the correct training labels for the stage 2 models.

Figure 8:
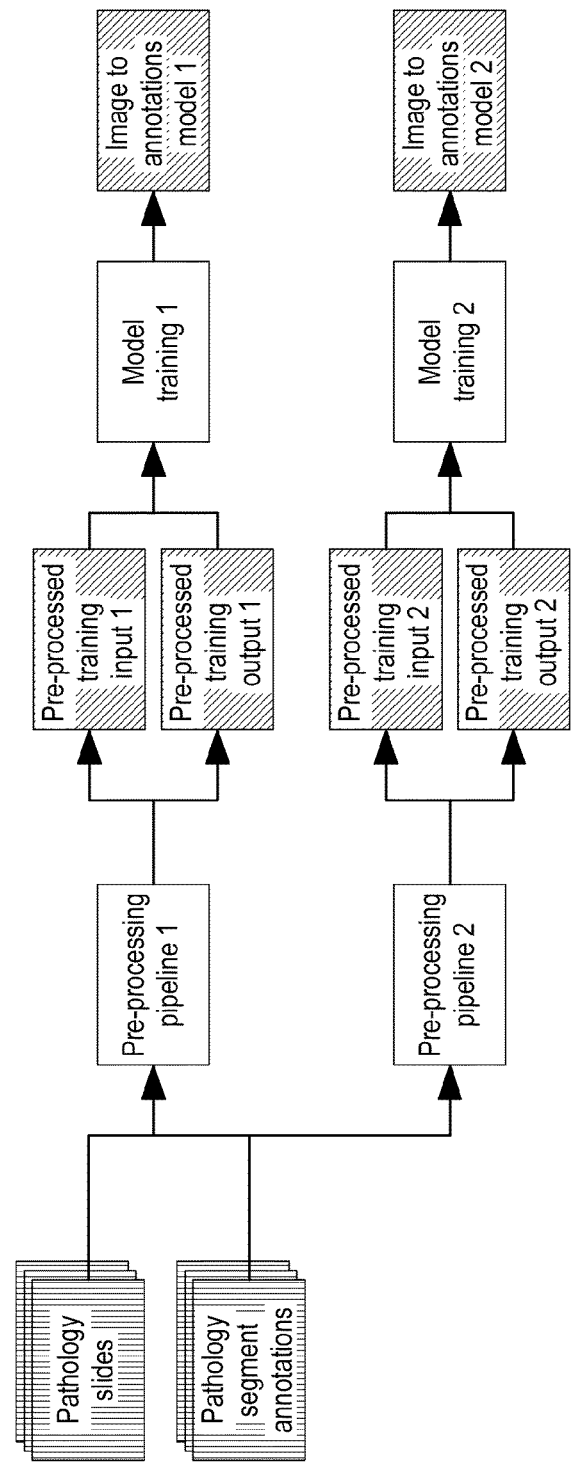
FIG. 8 is a schematic illustration of a method of training an image processing system in accordance with an embodiment.

Each image to image model has various types of input and output pairs. Therefore a distinct image pre-processing routine can be implemented for each model in order to generate the training data. FIG. 8 shows an example of pre-processing and training of two image to image annotation models. The same image annotation data is processed separately to generate separate training labels for each model, labelled pre-processed training output 1 and pre-processed training output 2. The input image, in this case the pathology slides, is processed to generate the input data for each model. The input data for each model is the same, therefore pre-processed training input 1 is the same as pre-processed training input 2.

The input and output size of a DCNN is adjusted by adjusting the model architecture. The framework shown in FIG. 6(a) for example enables one model to be replaced with another DCNN model, for example an updated model, as long as the input and output of the entire network are the same. The input and output of the hidden layers within the models does not have to have the same dimensions.

In the above description, examples are described in which multiple image to image models are stacked in parallel. However, additionally or alternatively, multiple image to image models can be stacked sequentially in the first stage. For example, the output of a first image to image model may feed into a second image to image model. The output of the second image to image model then feeds into the second stage. The output of the first image to image model may be applied as a mask to the original image, and then the masked image taken as input to the second image to image model. In an embodiment, a first image to image model detects regions of interest within the image. The output of this model is then applied to the original image as a mask. The masked image is then input into a second image to image model, which identifies mitotic cell regions for example. By combining the models sequentially, the features identified may be traced through the process.

Multiple diagnosis models may additionally or alternatively be stacked sequentially in the second stage. For example, the output of a first diagnosis model may feed into a second diagnosis model.

The framework design enables the deployment of any architecture, as long as the shape of a network's input and output images matches the existing models. This means that the architecture of the image to image annotation networks can be updated to include more advanced architecture, by adjusting said architecture to have input and output dimensions matching those of the existing model. The flexible design allows models to be "plugged" into the pipeline. Updated models may therefore replace existing models as needed, meaning improved performance metrics can be achieved. The system can use a flexible multi-model, multi-context design.

Furthermore, a user can select which models to include on their IAS. This flexibility enables the user to design complex image analysis that suits their needs.

One or more annotation models are represented as DCNNs. The system is designed so that the model can be replaced with an alternative DCNN, for example an updated DCNN, as long as it has the same input and output dimension. The modular system supports this. The system provides a flexible framework for implementing various modes of analysis. For simpler analysis (for example DCIS Grading) an image-to-annotation followed by a diagnostic model can be used. For more complex use cases, a series of diagnostic models can be stacked, either sequentially or in parallel, to enable incorporation of various contexts of analysis.

Various use cases are possible. For example, applications such as annotation tool for cancer research, clinical cancer diagnostic and clinical trials are possible.

Further embodiments are set out in the following clauses:

1. A computer implemented method of processing an image of tissue, comprising:
   inputting image data comprising a plurality of pixels into a first trained model, the first trained model generating a value corresponding to each of a plurality of pixels representing a feature relevant to disease diagnosis;
   wherein the first trained model comprises a convolutional neural network comprising a layer in which a first filter and a second filter are applied, at least one of the first filter and the second filter comprising a dilated convolution, wherein the output of the first filter and the second filter are combined and input into the subsequent layer.

2. The method according to clause 1, wherein the convolutional neural network comprises at least one skip connection.

3. The method according to clause 1 or 2, wherein the first filter is a dilated convolution having a first dilation factor and the second filter is a dilated convolution having a second dilation factor.

4. The method according to any preceding clause, further comprising:
   receiving modified data generated by a user editing one or more output values via a graphical user interface;
   adapting the first trained model using the modified data.

5. The method according to any preceding clause, further comprising:
   generating multiple versions of the modified data;
   adapting the first trained model using the multiple versions.

6. A computer implemented method of processing an image of tissue, comprising:
   inputting image data into a first trained model comprising a convolutional neural network, the first trained model generating a first set of output data representing a feature of the image relevant to disease diagnosis;
   inputting image data into a second trained model comprising a convolutional neural network, the second trained model generating a second set of output data representing a feature of the image relevant to disease diagnosis;
   combining the first set of output data and the second set of output data;
   generating diagnostic information from the combined data using a third trained model.

7. The method according to any preceding clause, wherein the value indicates one of the following features: regions of interest in the image, coordinates of dividing cells, or segments of various tissues.

8. The method according to any of clauses 6 to 7, wherein the diagnostic information comprises one or more of: a cancer tissue nucleation index, a mitotic index, a grading, an indication of tumour size, a metastatic index, or a nodal index.

9. A computer implemented method of disease diagnosis, comprising a method of processing an image of tissue according to any of clauses 6 to 8, further comprising:
   generating a diagnosis from the diagnostic information and context information using a fourth trained model.

10. A computer implemented method of training a system for processing an image of tissue, comprising:
    inputting training image data comprising a plurality of pixels into a first model, the first model generating a value corresponding to each of a plurality of pixels representing a feature relevant to disease diagnosis;
    wherein the first model comprises a convolutional neural network comprising a layer in which a first filter and a second filter are performed, at least one of the first filter and the second filter being a dilated convolution, wherein the output of the first filter and the second filter are combined and input into the subsequent layer;
    training the first model using training data labels.

11. A computer implemented method of training a system for processing an image of tissue, comprising:
inputting training image data into a first model comprising a convolutional neural network, the first model generating a first set of output data representing a feature of the image relevant to disease diagnosis;
inputting training image data into a second model comprising a convolutional neural network, the second model generating a second set of output data representing a feature of the image relevant to disease diagnosis;
generating diagnostic information from training data using a third model;
training the first model using training data labels;
training the second model using training data labels;
training the third model using training data labels.

12. A system for processing an image of tissue, comprising:
an input;
an output;
a processor configured to:
input received image data comprising a plurality of pixels into a first trained model, the first trained model generating a value corresponding to each of a plurality of pixels representing a feature relevant to disease diagnosis;
wherein the first trained model comprises a convolutional neural network comprising a layer in which a first filter and a second filter are performed, at least one of the first filter and the second filter being a dilated convolution, wherein the output of the first filter and the second filter are combined and input into the subsequent layer.

13. A system for processing an image of tissue, comprising:
an input;
an output;
a processor configured to:
input received image data into a first trained model comprising a convolutional neural network, the first trained model generating a first set of output data representing a feature of the image relevant to disease diagnosis;
input the received image data into a second trained model comprising a convolutional neural network, the second trained model generating a second set of output data representing a feature of the image relevant to disease diagnosis;
combine the first set of output data and the second set of output data;
generate diagnostic information from the combined data using a third trained model.

14. The system of any of clauses 12 to 13, wherein the input comprises a microscope and a digital imaging device configured to capture images of tissue through the microscope.

15. A carrier medium comprising computer readable code configured to cause a computer to perform the method of any of clauses 1 to 11.

While certain embodiments have been described, these embodiments have been presented by way of example only, and are not intended to limit the scope of the inventions. Indeed the novel methods and apparatus described herein may be embodied in a variety of other forms; furthermore, various omissions, substitutions and changes in the form of methods and apparatus described herein may be made.

The invention claimed is:

1. A computer implemented method of processing an image of tissue, comprising:
inputting image data corresponding to the image of tissue into a first trained model comprising a convolutional neural network, the first trained model generating a first set of output data, wherein the first set of output data represents a feature of the image relevant to disease diagnosis;
inputting the image data corresponding to the image of tissue into a second trained model comprising a convolutional neural network, the second trained model generating a second set of output data, wherein the second set of output data represents a feature of the image relevant to disease diagnosis;
combining the first set of output data and the second set of output data;
generating diagnostic information from the combined data using a third trained model; and
generating a diagnosis from the diagnostic information and context information using a fourth trained model.

2. The method according to claim 1, wherein the first or second set of output data indicates one of the following features: regions of interest in the image, coordinates of dividing cells, or segments of various tissues.

3. The method according to claim 1, wherein the diagnostic information comprises one or more of: a cancer tissue nucleation index, a mitotic index, a grading, an indication of tumour size, a metastatic index, or a nodal index.

4. The method according to claim 1, wherein the image data comprises pixel data, and wherein the pixel data is directly input into the convolutional neural network of the first trained model and is directly input into the convolutional neural network of the second trained model.

5. The method according to claim 1, wherein the first trained model is an image to image model and the second trained model is an image to image model.

6. The method according to claim 1, wherein the convolutional neural network of the first trained model comprises a layer in which a first filter and a second filter are applied, at least one of the first filter and the second filter comprising a dilated convolution, wherein the output of the first filter and the second filter are combined and input into the subsequent layer, and wherein the convolutional neural network of the second trained model comprises a layer in which a third filter and a fourth filter are applied, at least one of the third filter and the fourth filter comprising a dilated convolution, wherein the output of the third filter and the fourth filter are combined and input into the subsequent layer.

7. The method according to claim 6, wherein the convolutional neural network of the first trained model comprises at least one skip connection and the convolutional neural network of the second trained model comprises at least one skip connection.

8. The method according to claim 6, wherein the convolutional neural network of the first trained model comprises a first layer configured to generate an output having a dimension smaller than the output of a previous layer, and a second layer subsequent to the first layer, wherein the input to the second layer is generated from the input to the first layer or a layer prior to the first layer and the output of the layer prior to the second layer, and wherein the convolutional neural network of the second trained model comprises a third layer configured to generate an output having a dimension smaller than the output of a previous layer, and a fourth layer subsequent to the third layer, wherein the input to the fourth layer is generated from the input to the third layer or a layer prior to the third layer and the output of the layer prior to the fourth layer.

9. The method according to claim 6, wherein the first filter is a dilated convolution having a first dilation factor and the second filter is a dilated convolution having a second dilation factor.

10. The method according to claim 9, wherein the convolutional neural network comprises at least one skip connection.

11. The method according to claim 9, wherein the convolutional neural network comprises a first layer configured to generate an output having a dimension smaller than the output of a previous layer, and a second layer subsequent to the first layer, wherein the input to the second layer is generated from the input to the first layer or a layer prior to the first layer and the output of the layer prior to the second layer.

12. The method according to claim 1, wherein the image data comprises a plurality of pixels, and wherein the first trained model generates a value corresponding to each of a plurality of pixels representing the feature relevant to disease diagnosis.

13. The method according to claim 12, further comprising:
   receiving modified data generated by a user editing one or more output values via a graphical user interface;
   adapting the first trained model using the modified data;
   generating multiple versions of the modified data; and
   adapting the first trained model using the multiple versions.

14. A computer implemented method of training a system for processing an image of tissue, comprising:
   inputting training image data into a first model comprising a convolutional neural network, the first model generating a first set of output data, wherein the first set of output data represents a feature of the image relevant to disease diagnosis;
   inputting training image data into a second model comprising a convolutional neural network, the second model generating a second set of output data, wherein the second set of output data represents a feature of the image relevant to disease diagnosis;
   generating diagnostic information from training data using a third model;
   generating a diagnosis from the diagnostic information and context information using a fourth model;
   training the first model using training data labels;
   training the second model using training data labels;
   training the third model using training data labels; and
   training the fourth model using training data labels.

15. A system for processing an image of tissue, comprising:
   an input for receiving image data corresponding to the image of tissue;
   an output for outputting diagnostic information;
   a processor configured to:
      input received image data corresponding to the image of tissue into a first trained model comprising a convolutional neural network, the first trained model generating a first set of output data, wherein the first set of output data represents a feature of the image relevant to disease diagnosis;
      input the received image data corresponding to the image of tissue into a second trained model comprising a convolutional neural network, the second trained model generating a second set of output data, wherein the second set of output data represents a feature of the image relevant to disease diagnosis;
      combine the first set of output data and the second set of output data;
      generate diagnostic information from the combined data using a third trained model; and
      generate a diagnosis from the diagnostic information and context information using a fourth trained model.

16. The system of claim 15, wherein the input comprises a microscope and a digital imaging device configured to capture images of tissue through the microscope.

17. A non-transitory computer readable storage comprising computer readable code configured to cause a computer to perform the method of claim 1.

* * * * *